United States Patent [19]

Gelfand et al.

[11] Patent Number: 4,666,848
[45] Date of Patent: May 19, 1987

[54] POLYPEPTIDE EXPRESSION USING A PORTABLE TEMPERATURE SENSITIVE CONTROL CASSETTE WITH A POSITIVE RETROREGULATORY ELEMENT

[75] Inventors: David H. Gelfand, Oakland; Shing Chang, Hercules; Hing C. Wong, San Ramon, all of Calif.

[73] Assignee: Cetus Corporation, Emeryville, Calif.

[21] Appl. No.: 646,709

[22] Filed: Aug. 31, 1984

[51] Int. Cl.[4] .................. C12N 1/20; C12N 15/00; C12N 1/00; C12R 1/19
[52] U.S. Cl. .................. 435/253; 435/172.3; 435/243; 435/317; 435/849; 935/6; 935/8; 935/36; 935/39
[58] Field of Search .................. 435/172.3, 317, 243, 435/253, 849; 935/29, 39, 6, 8, 36

[56] References Cited

U.S. PATENT DOCUMENTS 4,448,885 5/1984 Schneff et al. .................. 435/253
4,518,584 5/1985 Mark et al. .

OTHER PUBLICATIONS

Maniatis et al. In *Molecular Cloning, A Laboratory Manual*, Cold Spring Harbor, 1982, pp. 405-411.
Boneigi et al, Cell 27:299-308, 1981.
Uhlin et al., Gene 6: 91-106, 1979.
Taniguchi et al., Nature 302:305-310, 1983.

*Primary Examiner*—Alvin E. Tanenholtz
*Attorney, Agent, or Firm*—Albert P. Halluin; Elliott L. Fineman

[57] ABSTRACT

The invention is a plasmid vector in which a first DNA sequence expressionable for a selected gene product is ligated to a positive retroregulatory element in a relationship thereto whereby expression of the selected gene product is enhanced. The first DNA sequence is furthermore operably linked to a second and third DNA sequence operably linked to one another which are respectively the $P_L$ promoter and a DNA sequence corresponding to an N gene ribosome binding site. Microorganisms transformed with the plasmid are also claimed.

17 Claims, 6 Drawing Figures

POTENTIAL SECONDARY STRUCTURE AT THE 3'-END OF THE cry mRNA $\Delta G = -30.4$ Kcal POTENTIAL SECONDARY STRUCTURE AT THE 3'-END OF THE cry mRNA TRANSCRIPTIONAL FUSION OF THE penP AND THE cry TRANSCRIPTIONAL TERMINATOR E-EcoRI, B-BamHI, H-HindIII, P-PvuII, S-SalI TRANSCRIPTIONAL FUSIONS OF THE HUMAN IL-2 GENE AND THE *cry* TRANSCRIPTIONAL TERMINATOR ⚲: The *cry* Transcriptional Terminator E-EcoRI, H-HindIII, B-BamHI, P-PvuII, A-AvaI, S-StuI

POLYPEPTIDE EXPRESSION USING A PORTABLE TEMPERATURE SENSITIVE CONTROL CASSETTE WITH A POSITIVE RETROREGULATORY ELEMENT

FIELD OF THE INVENTION

The invention concerns the field of recombinant DNA. More particularly the invention concerns positive retroregulatory elements, which when ligated to selected DNA sequences coding for a gene product, enhance the expression of the gene product. Plasmids carrying the positive retroregulatory element ligated to selected DNA sequence and cells transformed by such plasmids are provided. In addition, the invention relates to a method for enhancing expression of a gene product by ligating a positive retroregulatory element to a selected DNA sequence expressionable for a desired gene product.

One of the fundamental stratagies forming the basis for the commercial utility of recombinant DNA technology is the production in relatively high volumes of gene products in the form of polypeptides or proteins that ordinarily occur in nature at very low concentrations or volume. By transforming cells that have relatively short generation or doubling times with recombinant molecules, which generally are in the form of plasmids, significant amounts of a desired gene product may be produced. Although each cell harboring the recombinant DNA molecule may in fact produce only a very small amount of the desired gene product, the rapid multiplication of the cell allows the production of significant amounts of the desired gene product.

In general, the goal of producing larger amounts of a selected gene product is limited by the size of culture medium volumes required for growing the transformed cell that produces the desired gene product. Increasing the yield of a desired gene product is clearly a major concern in the commercial production of a desired gene product. One approach to increasing yield is to improve the recovery rate of the desired gene product from the transformed cell or culture medium while leaving the amount of product produced by the cell unchanged. This approach entails the addition of processing steps to increase recovery of the desired gene product from a given fermentation run. Such additional processing steps can require enormous costs for added equipment and personnel.

A different approach to increasing yield of a desired gene product is to increase the expression of the desired gene product by the transformed cell. Such increases in production of the desired gene product by each cell can lead to increases in yield for a particular fermentation run as well as improvements in purity of the product produced and a lowering of the cost per unit of product since further processing may be unnecessary.

One of the important general approaches to improving the yield of desired gene product per cell is to provide optimal culture conditions for the cell. By enriching the nutrient content of the medium, providing optimal temperatures for fermentations, furnishing the optimum amount of trace factors and supplementing the culture medium with required amino acids, for example, yields can be significantly improved.

A second general approach to the problem of increasing the yield of a desired gene product per cell is to manipulate the regulatory elements controlling the expression of the gene product by the cell. One method of manipulating the regulatory elements controlling expression of a desired gene product is by the selection of strong promoters. Promoters may be generally defined as regions of a DNA molecule to which RNA polymerase binds to initiate transcription of messenger RNA (mRNA) from a DNA sequence coding for a gene product. Strong promoters have the characteristic of initiating an RNA transcript by RNA polymerase with higher frequency than weaker promoters with the result that the DNA sequence with which the promoter is associated is transcribed to form more mRNA transcript coding for the desired gene product.

It has become conventional in the recombinant DNA field to ligate a strong promoter to a selected DNA sequence coding for a desired gene product, in proper reading frame such that mRNA transcripts, initiated from the strong promoter are produced. Multiple strong promoters may be ligated to a selected DNA sequence, thereby increasing the opportunity for binding RNA polymerase to the DNA sequence and producing more mRNA transcript from the DNA sequence. An example of this last method is the use of tandam lac operon promoters at the beginning of a DNA sequence coding for a desired gene product.

Another approach for increasing the binding of RNA polymerase to provide higher levels of mRNA transcript is the elimination of regulatory factors that tend to reduce the ability of RNA polymerase to transcribe mRNA from a DNA sequence coding for a desired gene product. Certain strong promoters have associated with them attenuator regions which under certain conditions cause a bound RNA polymerase to cease transcription of DNA sequences with which the attenuator regions are associated. One such attenuator region is associated with the promoter of the tryptophan operon, a promoter which is known to be a strong promoter. By eliminating the attenuator region of the promoter of the tryptophan operon, the tryptophan promoter can serve as an unimpaired strong promoter.

Another approach to increasing the yield of a desired gene product is to ligate strong ribosome binding sites within a selected DNA sequence such that ribosomes bind with high efficiency to the mRNA transcript that has been transcribed from the selected DNA sequence. By increasing the affinity of an mRNA transcript for the ribosome through such strong ribosome binding sites, it is believed translation of the mRNA transcript occurs with a greater frequency, thus increasing the production of the desired gene product.

All of the above-mentioned techniques for increasing the expression of a desired gene product involve manipulation of regulatory sequences that appear at the 5' end of the DNA sequence coding for the desired gene product. In all cases, these regulatory sequences are involved in either initiation of transcription of the DNA sequence coding for the desired gene product, or initiation of translation of the mRNA transcript corresponding to the DNA sequence coding for the desired gene product.

Another form of regulation of the expression of a gene has been observed in various viral systems. The term "retroregulation" has been coined for this form of expression control. Court et al. infra (1983). As described in the prior art, the known form of retroregulation is uniformly found to decrease the expression of the gene product on which the retroregulator exerts its effect. Thus, known forms of retroregulation are negative retroregulation.

In bacteriophage λ, the regulation of the expression of the integrase gene (int) mRNA sequence by a 3'-terminal sequence designated sib, is described in Schindler and Echols, "Retroregulation of the int gene of bacteriaphage λ: Control of translation completion", *Proc. Natl. Acd. of Sci. (USA)*, 78: 4475–4479 (1981). Schindler and Echols postulate that the sib region acts at the translation level of expression by preventing normal completion of protein synthesis from int mRNA. It is further postulated that the sib regulatory region corresponds to an mRNA region which is able to form a stem and loop secondary structure duplex. The sib region also is believed to include a region near the end of the gene which it regulates that provides a cleavage site for RNase III. This cleavage site for RNase III renders the mRNA sensitive to degradation by various exonucleases. The authors postulate that by degrading the mRNA transcript, protein synthesis of the int gene product is prematurely terminated. Thus, the reference discloses a negative regulatory role for the sib regulatory sequence, whereby the production of the polypeptide encoded by the int gene is decreased. Guarneros et al., Posttranscriptional Control of Bacteriophage λ int Gene Expression From a Site Distal to the Gene, *Proc. Natl. Acd. of Sci. (USA)*, 79: 238–242 (1982) discloses that in bacterial hosts which lack functional RNase III, sib regulation is defective. The reference further concurs with Schindler and Echols, surpa, that the sib retroregulatory element functions post-transcriptionally to prevent mRNA translation by increasing the degradation of int mRNA. Court et al., Detection Analysis of the Retroregulatory Site for the λ int Gene, *J. Mol. Biol.*, 166: 233–240 (1983) concurs with the general teachings of Guarneros et al. supra and further suggests that the RNase III sensitive structure of the retroregulatory element encoding the sib site is similar to other RNase III sensitive sites found in *Escherichia coli* and phage.

In a general discussion of termination of transcription in *E. coli*, Holmes et al., Termination of Transcription in *E. coli, Cell*, 32: 1029–1032 (1983), discloses that the primary structure of DNA sequences coding for transcription terminators includes runs of adenine and thymine base pairs on either side of symmetrical guanine-cytosine rich sequences. mRNA transcripts from these sequences form secondary hairpin loop or stem and loop structures which are followed by runs of uradine residues of either side. Such terminators function as terminators in either orientation. The reference, however, emphasizes that the significance of this bidirectional terminator activity is unclear. The reference also discusses the fact that RNA transcripts of DNA sequences coding for transcription terminators that lack a stem and loop structure, are degraded more rapidly than terminators having such structures. Platt and Bear in "Role of RNA Polymerase, ρFactor and Ribosomes in Transcription Termination", *Gene Function in Prokaryots*, Beckwith, et al. eds., Cold Spring Harbor Laboratory, N.Y. (1983) generally reviews transcription termination and the role of secondary structures at the end of RNA transcripts in the regulation of transcription termination. The authors speculate on the possibility of several functions for secondary structures in mRNA, one of which includes the stabilization from degradation beyond a certain point by 3' exonucleases of completed mRNA transcripts. There is, however, no suggestion that enhancement of expression of the gene product for which the mRNA transcript codes is obtained.

Gentz, R., Cloning and Analysis of strong promoters is made possible by the downstream placement of a RNA termination signal, *Proc. Natl. Acad. of Sci. (USA)*, 78: 4936–4940 (1981) shows that in plasmid pLBU3, addition of a strong transcription terminator derived from the bacteriophage fd, to the alpha fragment of the β-galactosidase gene which lacked the lac promoter region, made possible the cloning of strong promoters for phage T5. Strong promoters were isolated by increased β-galactosidase activity in an M15 (a lac α fragment deletion mutant) complementation assay. Strong transcription termination activity was shown by the fd terminator, which has a region of dyad symmetry, but this strong transcription termination activity was only reported in an orientation opposite to its native orientation in the fd genome in the system described by Gentz et al. The fd fragment is pLUB3, unlike its activity in the fd genome, cooperates with ρ factor to terminate transcription efficiently. There is however no teaching, nor is any evidence shown by Gentz et al., that the fd transcription terminator itself has an enhancing effect on expression of the β-galactosidase gene. Gentz et al. attribute the assayable β-galactosidase activity to the strong promoters derived from phage T5 which are ligated to 5' end of the DNA sequence coding for the α fragment of the β-galactosidase gene.

Flock et al., Expression in *Bacillus subtilis* of the gene for human urogastrone using synthetic ribosome binding sites, *Molecular and General Genetics*, 195: 246–251 (1984) state that "placing a transcription terminator from bacteriophage fd immediately after the urogasterone gene in (plasmid) pFF810 improves the overall expression about 5–10 times in *E. coli*." No details of which fd transcription terminator signal, its sequence, orientation or placement relative to immediate end of the urogasterone gene are given. The fd transcription terminator of Flock et al. is used in conjunction with a putatively strong promoter which is expected to be highly active in *B. subtilis*.

In some bacteria relatively stable high copy number mRNAs have been observed that appear to be associated with bacterial proteins or lipoproteins that occur in large amounts. For example, it has been reported that mRNA from the cry gene of *Bacillus thuringiensis* has a longer half-life than other mRNAs of genes expressed during sporulation. Petit-Galtron, M. F. and Rapoport, G., Translation of a stable mRNA fraction from sporulating cells of *B. thuringiensis* in a cell-free system from *E. coli, Biochimie*, 58: 119–129 (1976). This increased mRNA stability has long been speculated as the contributing factor for the massive synthesis of the crystal protein during sporulation.

In addition, the mRNA from the lipoprotein (lpp) gene of *E. coli* which directs the synthesis of a major outer membrane protein is known to be relatively stable and has been shown to have sequences capable of forming extensive secondary structures in the form of stem and loop structures having $\Delta G°$ values ranging from about $-0.4$ to about $-21.1$ kcal/mole. Nakamura, K. et al., Messenger ribonucleic acid of the lipoprotein of the *E. coli* outer membrane II. The complete nucleotide sequence, *J. Biol. Chem.*, 255: 210–216 (1980). Neither Nakumura et al. nor Petit-Galtron et al. suggest that these structures may be used to enhance expression of a desired gene product. Moreover, the nucleotide sequence for the cloned cry gene, as will be shown hereinbelow, lacks the extensive secondary structure associated with the mRNA of the lpp gene.

In summary, the prior art with respect to retroregulation in general, shows that known retroregulatory sequences have a negative effect on the expression of the gene which they retroregulate. With respect to terminators, Gentz et al. and Flock et al. indicate that in association with a DNA sequence under the control of a strong promoter, effective expression of the gene for which the DNA sequence codes may be obtained, but that in the absence of such strong terminators the activity of a putative strong promoter cannot be clearly demonstrated.

DESCRIPTION OF THE INVENTION

The inventors have discovered positive retroregulatory elements which, when ligated to a DNA sequence coding for a selected gene product, significantly increase the production of the selected gene product.

As used herein, the term "selected" or "desired gene product" is meant to denote a polypeptide or protein produced by a prokaryotic or eukaryotic host by virtue of its transformation with a recombinant DNA molecule comprising a DNA sequence coding for the polypeptide or protein. Such a selected or desired gene product may be one otherwise ordinarily produced by the host, by a prokaryotic organism other than the host, or by a eukaryotic organism other than the host. The term "gene" as used herein means a DNA sequence coding for a polypeptide or protein. The term "expression" as used hereinbelow refers to the production of a polypeptide or protein coded for by a DNA sequence or gene. In general, the positive retroregulatory element is ligated downstream of the DNA sequence coding for the selected gene product. As used herein, the term "downstream" is used with respect to the direction of transcription of the messenger RNA to which the DNA sequence corresponds, transcription proceeds from upstream to downstream.

The location of the positive retroregulatory element is generally 3' to the end of the coding strand of the DNA sequence coding for the selected gene product. It is well known that in order for a gene to be expressed, a translation termination codon is usually found at the 3' end of the DNA sequence coding for the selected gene product. Typically, the positive retroregulatory element is ligated to a DNA sequence coding for a selected gene product 3' to the translation termination sequence associated with the DNA sequence for the selected gene. Known translation termination sequences generally are nucleotide triplets. An example of such translation termination codons include those having the sequence TAG, TAA, and TGA, wherein the letters correspond to thymine, adenine and guanine residues which are components of the DNA molecule. Translation termination codons may appear singly, paired sequentially, or in pairs having a number of nucleotides in between. See for example Watson, J. D., *Molecular Biology of the Gene*, W. A. Benjamin, Inc., Menlo Park, CA (3rd ed. 1977). The translation termination signal may be native to the DNA sequence coding for the selected gene product or may itself be ligated at the 3' end of the DNA sequence coding for the selected gene product to provide a translation termination signal in a desired location.

The distance of the positive retroregulatory element from the 3' end of the gene to which it is ligated may be varied while still exerting a positive or enhancing effect on the expression of the gene. As will be explained in greater detail herein below, a particular region of the positive retroregulatory element isolated from the 3' flanking region of the gene coding for the *B. thuringiensis* crystal protein, which is believed to form a "stem and loop" structure at the end of the mRNA transcript for the selected gene, has been ligated from about 30 to about 300 nucleotides from the 3' end of the selected gene. In both constructions, a positive retroregulatory effect is shown on the expression of the gene to which the positive retroregulatory element was ligated.

As will be shown in detail in the examples hereinbelow, positive retroregulatory elements have been shown to enhance expression of the gene to which they are ligated irrespective of the orientation of the positive retroregulatory element. It has been shown that so long as the positive retroregulatory element is ligated at the 3' end of a selected gene, the positive retroregulatory element may have a 3'-5' orientation or a 5'-3' orientation and still exert an enhancing effect on expression of the selected gene.

The positive retroregulatory element according to the invention may be characterized structurally as a DNA sequence which transcribes for a corresponding RNA transcript which is capable of forming a stem and loop structure having a Gibbs free energy constant ($\Delta G^\circ$) of about $-30.4$ Kcal as determined by the methods of Tinoco, I. et al., *Nature New Biology,* 246: 40–41 (1973). In one effective embodiment, the positive retroregulatory element according to the invention is a DNA sequence that transcribes for a corresponding RNA transcript that is capable of forming a stem and loop structure which has a guanine-cytosine residue content of about 43%. It is expected that such stem and loop structures having guanine-cytosine contents of from about 40% to about 45% will also be effective positive retroregulatory elements. Such positive retroregulatory elements are intended to be within the scope of the invention.

In a preferred embodiment of the invention, the positive retroregulatory element is characterized as a DNA sequence having an inverted repeat sequence including the deoxyribonucleotide sequence AAAACGGACAT-CACCTCCATTGAAACGGAGT-GATGTCCGTTTT wherein the underlined portion of the sequence comprises the inverted repeat sequence. The corresponding mRNA transcript for the above-mentioned inverted repeat sequence has the ribonucleotide sequence AAAACGGAAUCACCUCCAU-UGAAACGGAG UGAUGUCCGUUUU wherein the underlined portion of the ribonucleotide sequence is the inverted repeat sequence.

It is expected that some variants of the above-mentioned deoxynucleotide sequence and the corresponding RNA transcript which can arise either through random mutation, point mutation, addition mutation, deletion mutation, synthetic oligonucleotide directed mutagenesis or construction of synthetic oligonucleotides may have inverted repeated sequences that will preserve the positive retroregulatory effect of the positive retroregulatory element. Such variants that preserve the positive retroregulatory effect of the positive retroregulatory element are clearly within the scope of the invention.

As will be described in greater detail hereinbelow, the positive retroregulatory element according to the invention may be isolated from a portion of the 3′ flanking region of the gene coding for the *B. thuringiensis* crystal protein (cry gene). The 3′ flanking region may be purified using conventional gel electrophoresis techniques and cloned into an appropriate host for multiplication. In one embodiment of the invention, as further described hereinbelow in the examples, a portion of the 3′ flanking sequence of the cry gene which includes the transcription terminator signal thereof, was isolated, purified and cloned. This portion of the cry gene, about 382 nucleotides in length, includes a positive retroregulatory element as previously described hereinabove and portions of the 3′ flanking region of the cry gene thus have a positive retroregulatory effect.

When the positive retroregulatory element is ligated to a DNA sequence expressionable for a selected gene product in the proper relationship thereto, as described hereinabove, expression of the selected gene product is enhanced. Thus, the invention includes a method of enhancing expression of a selected gene product. As used herein the term "DNA sequence expressionable for a selected gene product" is intended to mean a selected gene, for example betalactamase or interleukin-2, having associated therewith a promoter, transcription start signal, ribosome binding site, translation start signal and translation termination signal all the proper relationship and reading frame such that the product for which the DNA sequence codes may be expressed. Numerous appropriate promoters are well known to those skilled in the art to which the invention pertains, and include: promoters derived from *E. coli* including the tryptophan promoter, lac promoter-operator and numerous other promoters well known to those skilled in the art; Bacillus promoters including the penP promoter; and various viral promoters such as for example the Sp82 promoter and PL promoter of phage λ. Viral promoters may be recognized by various cells depending upon the particular cell it ordinarily infects. The selected DNA sequence may further include a signal sequence, for example, the penP signal sequence such that the expressed gene product is secreted. If the selected DNA including a signal sequence is expressed in *E. coli,* the gene product will generally be secreted into the periplasmic space of the cell, and can be released from the periplasmic space by sonication. If the selected DNA including a signal sequence is expressed by *B. subtilis* for example, the selected gene product will generally be secreted into the culture medium and may be recovered therefrom.

The term "DNA sequence expressionable for a selected gene product" is furthermore intended to include factors required for expression of the gene product for which the DNA sequence codes, such as enzymes including functional RNA polymerase, transfer RNAs, amino acids, ribosomes and other elements necessary for the transcription and translation of the selected DNA sequence.

From the foregoing it will be understood that a "DNA sequence expressionable for a selected gene product" includes a vector such as a plasmid and a host cell transformed thereby which is capable of expressing the gene and forming the gene product coded by the gene. Examples of such plasmids and hosts are well known to those skilled in the art and are exemplified in detail in the examples hereinbelow. Among appropriate hosts for plasmids carrying a DNA sequence expressionable for a selected gene product are prokaryotic and eukaryotic cells. Prokaryotes may be defined as organisms that lack a true nucleus, the nuclear membrane being absent and the nuclear structures being collected in a nuclear region or nucleoid. The chromosomes of prokaryote are generally not associated with proteins.

Among appropriate prokaryotic cells as hosts for plasmids are both Gram-positive and Gram-negative bacteria. By the terms Gram-positive and Gram-negative is meant cells capable of taking up and retaining Gram stain and cells incapable of retaining Gram stain respectively. Among appropriate Gram-positive bacteria are those belonging to the genus Bacillus and in particular *B. subtilis. B. subtilis* strain PSL1 (BGSC number IA510) are particularly preferred.

Among appropriate Gram-negative bacteria are those belonging to the genus Escherichia, and in particular *E. coli* strain MM294 and CS412.

Eukaryotic cells may be defined as cells having a true nucleus bound by a nuclear membrane within which are found chromosomes usually bound to proteins. Included in eukaryotic cells are plant animal and fungal cells. Among the fungal cells are yeasts, and in particular Saccharomyces and especially *Saccharomyces cerevisiae* are useful in the practice of the invention.

Appropriate plasmids for carrying DNA sequences expressionable for a selected gene product are those capable of transforming a host cell such that the DNA sequence is expressed thereby. In general, a DNA sequence expressionable for a selected gene product ligated to a positive retroregulatory element may be placed in any plasmid capable of expressing the gene product in an appropriate transformed host. Thus the invention includes plasmids carrying DNA sequences expressionable for a selected gene product ligated to a positive retroregulatory element as well as the host cell transformed therewith.

Plasmids capable of transforming *E. coli* include for example Col E1 type plasmids in general. Other appropriate plasmids for transforming *E. coli* include: pSC101, pSF2124, pMB8, pMB9, pACYC184, pACYC177, pCK1, R6K, pBR312, pBR313, pBR317, pBR318, pBR320, pBR321, pBR322, pBR333, pBR341, pBR345, pBR350, pBR351, pML2, pML21, ColE1AP, RSF1010, pVH51, pVH151, and pVH153. See, *Recombinant Molecules Impact on Science and Society,* Beers, R. F. and Bassett, E. G., eds. Raven Press, New York (1977). The plasmids of the type pBR include pBR325, pBR327 and pBR328. See, Soberon et al., *Gene,* 9: 287–305 (1980). Other appropriate plasmids are described in *DNA Insertion Elements, Plasmids and Episomes,* Bukhari et al. (eds) Cold Spring Harbor Laboratory (1976).

Plasmids capable of transforming *B. subtilis* include: pC194, pC221, pC223, pUB112, pT127, pE194, pUB110, pSA0501, pSA2100, pTP4, pTP5 (see Gryczan, T. J., "Molecular Cloning in *B. subtilis* in *The Molecular Biology of the Bacilli,* Dubnau, D., Ed., Academic Press, Inc. New York, 1982, p. 310) and their derivatives.

Plasmids capable of transforming both *B. subtilis* and *E. coli* that may be used in the practice of the invention include: pDH5060, pLP1201 (Ostroff et al., infra, p062165 (Gray, O. and Chang, S., "Molecular cloning and expression of *B. licheniformis* β-lactamase gene in *E. coli* and *B. subtilis*", *J. Bacteriol.,* 145: 422–428 (1982), pHV11, pHV12, pHV14, pHV16 (Ehrlich, S. D., "DNA cloning in *B. subtilis*", *Proc. Natl. Acad. Sci.*

*USA*, 75: 1433–1436 (1978), and pSYC310-2 (McLaughlin et al., infra. See also Old, R. W. and Primrose, S. B., "Plasmid vectors for cloning in microbes other than *E. coli*", *Principles of Gene Manipulation* 2nd ed., Carr, N.6, Ingraham, L. L., and Rittenberg, S. C., Eds, University of Ca. Press, Berkeley, 1981, p. 48).

Plasmids capable of transforming *S. cerevisiae* include: pMP78, YEp13, pBTI1, pLC544, YEp2, YRp17, pRB8 (YIp30), pBTI7, pBTI9, pBTI10, pAC1, PSLe1, pJDB219, pDB248, and YRp7.

The DNA sequence coding for an expressionable gene product which is ligated to the positive retroregulatory element may be cistronic, i.e., coding for a single polypeptide or polycistronic, i.e., coding for a plurality of polypeptides, the mRNA for the polycistronic DNA being under the transcriptional control of a single promoter. Such polycystronic DNA sequences are well known to those skilled in the art and include, for example, the genes for tryptophan biosynthesis under the control of the tryptophan operon in *E. coli.* Polycistronic genes may also be artificially formed by ligating a series of desired genes together under the control of a single promoter. See for example Flock, J. et al., supra (1984).

The selected DNA sequence expressionable for a desired gene product ligated to a positive retroregulatory element may be homologous to the DNA of the host or alternatively heterologous to the DNA of the host. Thus, for example, the selected DNA sequence may be derived from an organism that is of the same species as the host cell that has been transformed to express the gene product, in which case, the selected DNA sequence as used herein is termed homologous. An example of an homologous gene sequence expressionable for a selected gene product according to the invention is the enhanced expression in an *E. coli* host transformed by a plasmid bearing a gene native to *E. coli.* An example is the production of *E. coli* β-galactosidase wherein the enhanced expression is mediated by the ligation of a positive retroregulatory element at the 3′ end of the β-galactosidase.

As mentioned above, the selected DNA sequence expressionable for a desired polypeptide ligated to a positive retroregulatory element may alternatively be heterologous to the host. Numerous examples of such heterologous enhanced expression are given in detail hereinbelow and include: the enhanced expression, under mediation of a positive retroregulatory element, of the *B. licheniformis* penicillinase gene in *B. subtilis;* eukaryotic genes such as mammalian interleukin-2 and mutated interleukin-2 in prokaryotic microorganisms such as *B. subtilis* and *E. coli.*

From the foregoing summary of the invention, it will be clear to those ordinarily skilled in the art that the inventors have provided positive retroregulatory elements, plasmids carrying the positive retroregulatory elements ligated to a DNA sequence expressionable for a selected gene product such that expression of the selected gene product is enhanced, cells which transformed by such plasmids express the selected gene product at enhanced levels, and the selected gene products so expressed.

It will furthermore be clear to those skilled in the art that the inventors have provided a general method for enhancing the expression of a selected gene product, the method comprising providing a DNA sequence expressionable for a selected gene product and ligating a positive retroregulatory element to the DNA sequence in a relationship thereto whereby expression of the selected gene product is enhanced. The general method, described hereinabove and in greater detail hereinbelow in the examples that follow, is effective to enhance expression of DNA sequences coding for a desired gene product in prokaryotic and eukaryotic hosts, and appears to be effective whether the DNA sequence to be expressed is homolgous or heterologous to the host cell that expresses it. The invention also includes the gene products produced by the general method for enhancing expression of a selected gene product.

The following examples are intended by the inventors to be merely exemplary of the invention and are not intended by the inventors to be limiting. As mentioned above, the invention described herein and claimed below is broadly applicable to the enhanced expression of numerous gene products by numerous cell types, a fact which will be readily apparent to the ordinarily skilled practitioner. The examples hereinbelow are merely intended to provide a detailed and practical description of the invention as applied to the cells and plasmids exemplified below.

Figure 1:
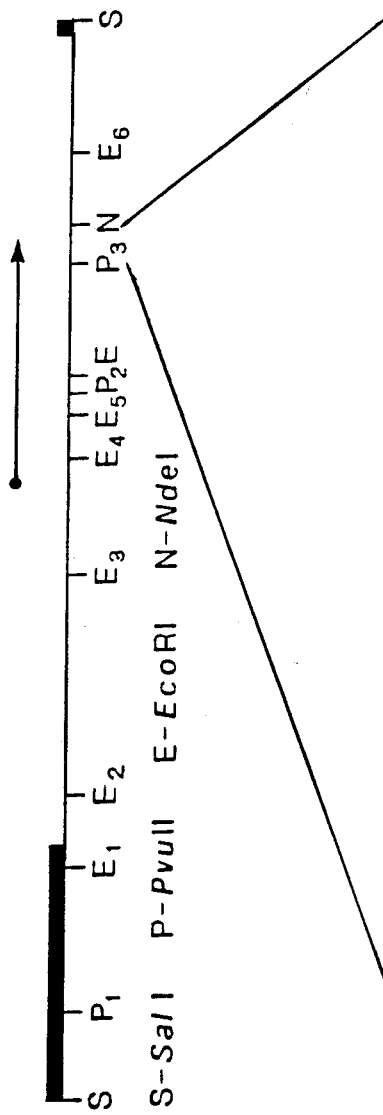
FIG. 1 is a schematic representation of the restriction map of the recombinant plasmid pES1 bearing the cloned cry gene from *B. thuringiensis.* Transcription of the crye gene originates at the site about 350 bp upstream of the fourth EcoRI site and terminates about 360 bp downstream of the third PvuII site shown in FIG. 1.

The nucleotide sequence of the PvuII-NdeI restriction fragment carrying the transcriptional terminator of cry is also shown in FIG. 1. There is a inverted repeat sequence located approximately 40-bp upstream of the NdeI site. An mRNA transcript made from this region can potentially form a stem and loop structure.

FIG. 2 shows the expected stem and loop structure of the RNA coded by the inverted repeat sequences indicated in FIG. 1. The stem-and-loop structure is relatively rich in G/C, about 44% G/C, with a predicted $\Delta G°$ of about $-30.4$ Kcal as calculated by the rules of Tinoco, et al., supra.

FIG. 3 is a schematic representation of plasmid pSYC667.

FIG. 4 is a schematic representation of plasmids pHCW701, pHCW702 and pLW1.

FIG. 5 is a schematic representation of plasmids pHCW300 and pHCW301 and the plasmids from which they were constructed.

FIG. 6 is a schematic representation of plasmid pFC54.t. None of the plasmids shown in the figure are intended to be scale drawings. Relative positions of endonuclease positions and relevant coding regions of the plasmids are depicted.

The following is a list of restriction endonucleases that were used in the examples appearing hereinbelow. The left column of the list is the commonly used name of the particular endonucleases and the right column is the organism from which it was originally derived. The listed restriction endonucleases were used under the buffer and temperature conditions recommended by the supplier. Restriction endonucleases are available from numerous commercial vendors including New England BioLabs, Beverly, Mass., USA and Bethesda Research Laboratories, Gaithersberg, Md. USA. The identity of the nucleotide sequences at which particular restriction endonucleases cut may be found in product catalogues of suppliers of the enzymes, as well as standard reference texts.
Figure 2:
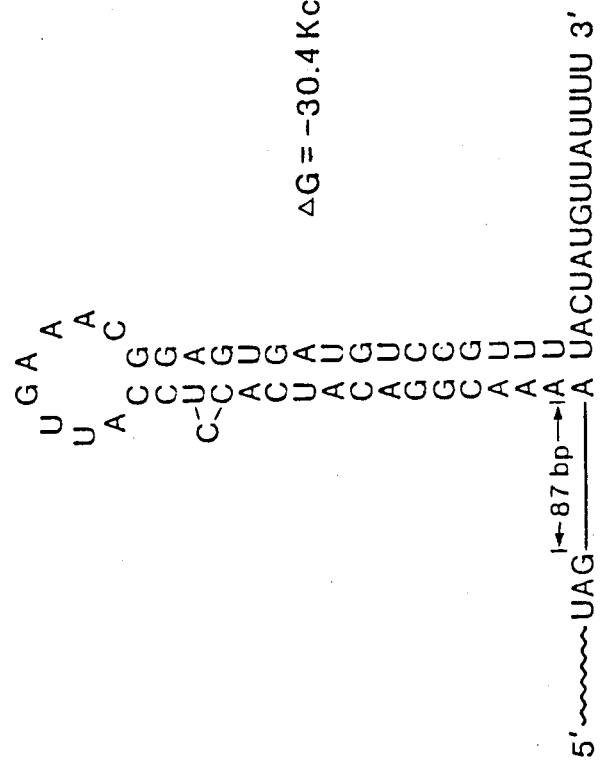

| Restriction Enconuclease | Organism Source |
|---|---|
| AvaI | *Anabaena variabilis* |
| AluII | *Arthobacter luteus* |
| BamHI | *Bacillus amyloliquefaciens* |
| BanII | *Bacillus aneurinolyticus* |
| BclI | *Bacillus caldolyticus* |
| ClaI | *Caryophanon latum* |
| EcoRI | *Escherichia coli* |
| HhaI | *Haemophilus haemolyticus* |
| HincII | *Haemophilus haemolyticus* |
| HindIII | *Haemophilus haemolyticus* |
| NdeI | *Neisseria denitrificans* |
| NruI | *Nocardia rubra* |
| PstI | *Escherichia coli* |
| PvuII | *Proteus vulgaris* |
| Sau3AI | *Staphylococcus aureus* |
| SmaI | *Serratia marcescens* |
| SphI | *Streptomyces phaeochromogenes* |
| StuII | *Steptomyces tubercidicus* |
| XbaI | *Xanthomonas badrii* |

Certain phrases and abbreviations are used herein. Unless otherwise noted, the meaning intended are as follows:

As used herein, the term "penP" is meant to denote the prepenicillinase gene of *B. licheniformis* strain 749/C, or, where clear from the context, a relevant portion thereof. The nucleotide sequence of penP has been published by Kroyer, J., and Chang, S., *Gene,* 15:343–347 (1981), and Neugebauer, K., Sprengel, R., and Schaller, H., *Nucl. Acids Res.,* 9: 2577–2589 (1981).

As used herein, "codon" means, interchangeably, (i) a triplet of ribonucleotides in an mRNA which is translated into an amino acid in a polypeptide or a code for initiation or termination of translation, or (ii) a triplet of deoxyribonucleotides in a gene whose complementary triplet is transcribed into a triplet of ribonucleotides in an mRNA which, in turn, is translated into an amino acid in a polypeptide or a code for initiation or termination or translation. Thus, for example, 5′-TCC-3′ and 5′-UCC-3′ are both "codons" for serine, as the term "codon" is used herein.

As used herein, "nucleotide", "deoxynucleotide", and "deoxyribonucleotide" all mean deoxyribonucleotide.

dNTP or NTP means any of the deoxyribonucleotide triphosphates, i.e., ATP, GTP, CTP or TTP.

"bp" means base pair, and "kb" means kilobase pairs.

"Polypeptide" means any peptide with two or more amino acids, including proteins.

"Coding sequence" or "DNA coding sequence" means a DNA sequence encoding a polypeptide.

"ATCC" means American Type Culture Collection, Rockville, Md. USA. When used in connection with a number, for example "ATCC 37017", ATCC refers to the American Type Culture Collection accession number for an organism on deposit with the ATCC.

"Operably linked" when used in regard to DNA sequence refers to the situation wherein the sequences are juxtaposed in such a manner so as to permit their ordinary functionality. For example, a promoter operably linked to a coding sequence refers to those linkages where the promoter is capable of controlling the expression of the sequence. The promoters operably linked to a ribosome binding coding sequence has the same significance: i.e., it permits the ribosome binding site (RBS) to be positioned in the transcript so as to participate in the initiation of the translation of the RNA transcript. An RBS operably linked to a start codon is positioned so as to permit the start of translation at this codon.

The methods of the present invention make use of techniques or genetic engineering and molecular cloning. General techniques of genetic engineering and molecular cloning are included in Maniatis, T., Fritsch, E. F., and Sambrook, J., *Molecular Cloning: A Laboratory Manual,* Cold Spring Harbor Laboratory, 1982, and *Methods in Enzymology,* Volume 68, Recombinant DNA, (Wu, R., editor), Academic Press, New York, 1979.

Oligonucleotide synthesis may be carried out by a number of methods including those disclosed in U.S. Pat. No. 4,415,734, and in Matteuci et al., *J. Am. Chem. Soc.,* 103 (11): 3185–3191 (1981), Adams et al., *J. Am. Chem. Soc.,* 105 (3): 661–663 (1983, and Bemcage et al., *Tetrahedron Letters,* 22 (20): 1859–1867 (1981).

EXAMPLE I

Preparation of 3′-Expression Enhancement Fragments

A. pES1

Plasmid pES1 was prepared as described in published European Patent Application Publication No. 82302137.3, which is herein incorporated by reference, from plasmid pBR322 (ATCC 37017) and a digest of the large plasmid fragment of *B. thuringiensis* var. Kurstaki HD-1. pES1 is also described in H. Schnepf and H. Witeley, *Proc. Natl. Acad. Sci.* (*USA*), 78: 2893–2897 (1981), and U.S. Pat. No. 4,448,885 which is herein incorporated by reference. pES1 in *E. coli* K-12/HB101 has been deposited by the assignee of the above-cited European application at the American Type Culture Collection, Rockville, Md. under the terms of the Budapest Treaty. The deposit number is ATCC 31995. *B. thuringiensis* var. Kurstaki strain HD-1-Dipel is available from the Northern Regional Research Laboratory Culture Collection in Peoria, Ill. under no. B3792. *B. thuringiensis* var. Kurstaki HD-1 is available from the American Type Culture Collection under accession number 1615.

As described in Schnepf and Whitely, supra, and in H. Wong et al., *Jour. Biol. Chem.,* 258, 1960 (1983), pES1 has inserted into the BamHI site on its pBR322 parent, a Sau3A1 fragment from the 30-megadalton plasmid, the 47-megadalton plasmid, or both such plasmids from *B. thuringiensis.* The Sau3A1 fragment includes a gene coding for the delta-endotoxin crystal protein of *B. thuringiensis* (cry gene). This gene is expressed to form a biologically active crystal protein in *E. coli* transformed with the plasmid pES1.

B. M13mp8 EP1-clone of 3′-end of cry gene

Plasmid pES1 was digested with PvuII and EcoRI and the resulting 2 kb fragment was isolated by agarose gel electrophoresis, Maniatis et al. supra 1982 p. 164 with the single exception that 1/10 X TEA (4 mM Tris. 0.1 mM Na EDTA $2H_2O$, 0.5 mM sodium acetate) was the buffer used. This fragment is from the 3′-end of the crystal protein gene and includes the transcription termination signal of the crystal gene. The map location and a portion of the sequence of the fragment, including the translation termination codon to just after the transcription termination signal, is shown in FIG. 1.

Using conventional ligation methods, the 2 kb fragment was then cloned into Replicative Form (RF) DNA of phage M13mp8 (available from Bethesada Research Laboratories Inc., Gaithersberg, Md., USA) that had been previously digested with SmaI and EcoRI. The resulting plasmid is designated M13mp8 EP1. *E. coli* strain JM103 was transformed with M13mp8 EP1 plasmid.

C. M13mp9 NP3-subclone of 3'-end of cry gene

M13mp9 NP 3 was prepared as follows: M13mp8 EP1 RF DNA was digested with NdeI. The NdeI ends were made blunt ended with *E. coli* DNA polymerase I Klenow fragment and dNTPs. The blunt ended DNA molecules were further digested with BamHI. A 382 base pair (bp) fragment designated NP3 carrying the transcription termination signal of the cry gene was then isolated by acrylamide gel electrophoresis using the method described in Maxim et al., *Proc. Natl. Acad. Sci. USA*, 74: 560-564 (1979). NP3 was subcloned into a BamHI-SmaI digested M13mp9 RF DNA to form M13mp9 NP3.

*E. coli* JM103 was transformed with M13mp9 NP3.

The fragment designed NP3 cloned into M13mp9 NP3 is shown in FIG. 1. As can be seen in the figure, the fragment cloned into M13mp9 NP3 lacks approximately 1.6 kb of DNA present between the NdeI and EcoRI sites downstream of the transcription termination signal in M13mp8 EP1.

EXAMPLE II

Synthetic Genes Comprising Positive Retroregulatory Elements

A. pSYC667

Figure 3:
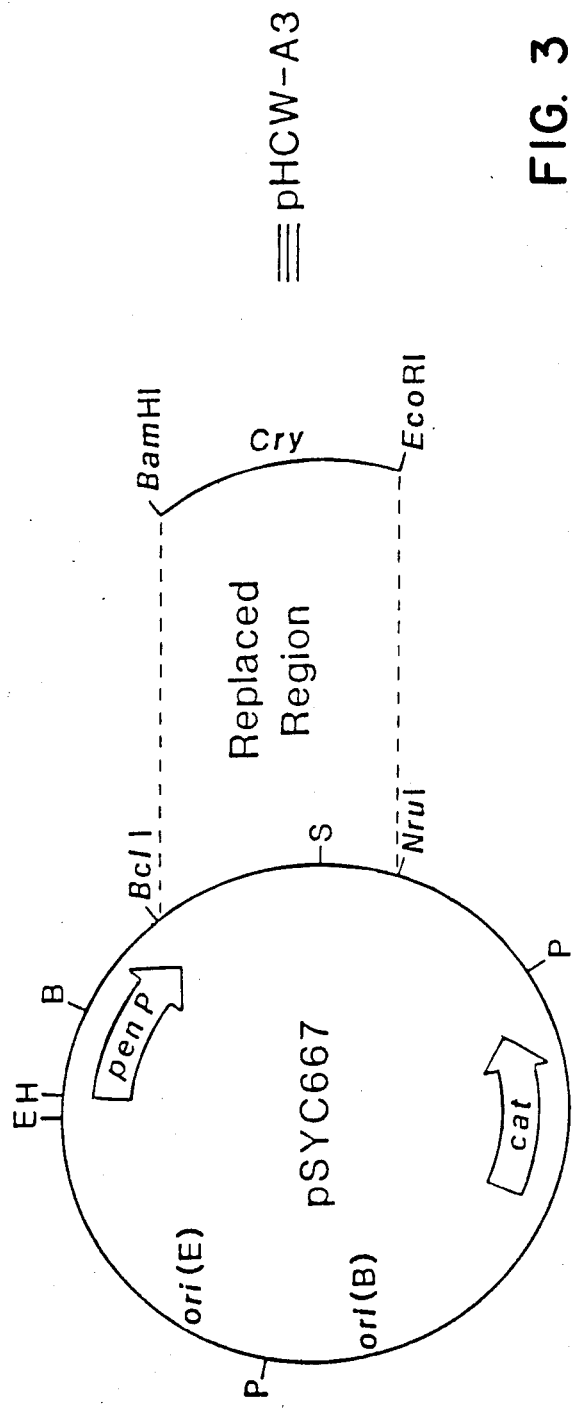
Figure 4:
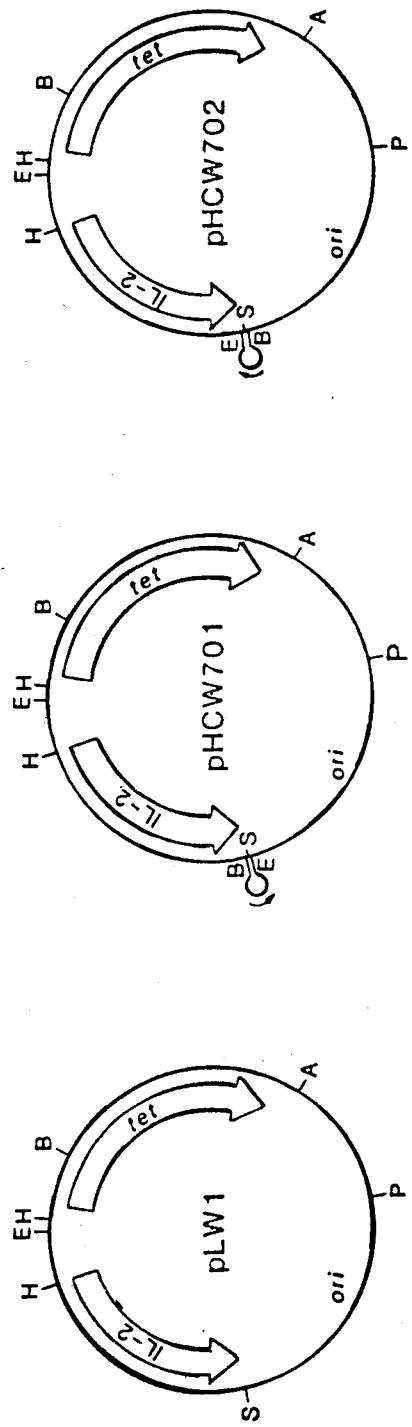
Figure 5:
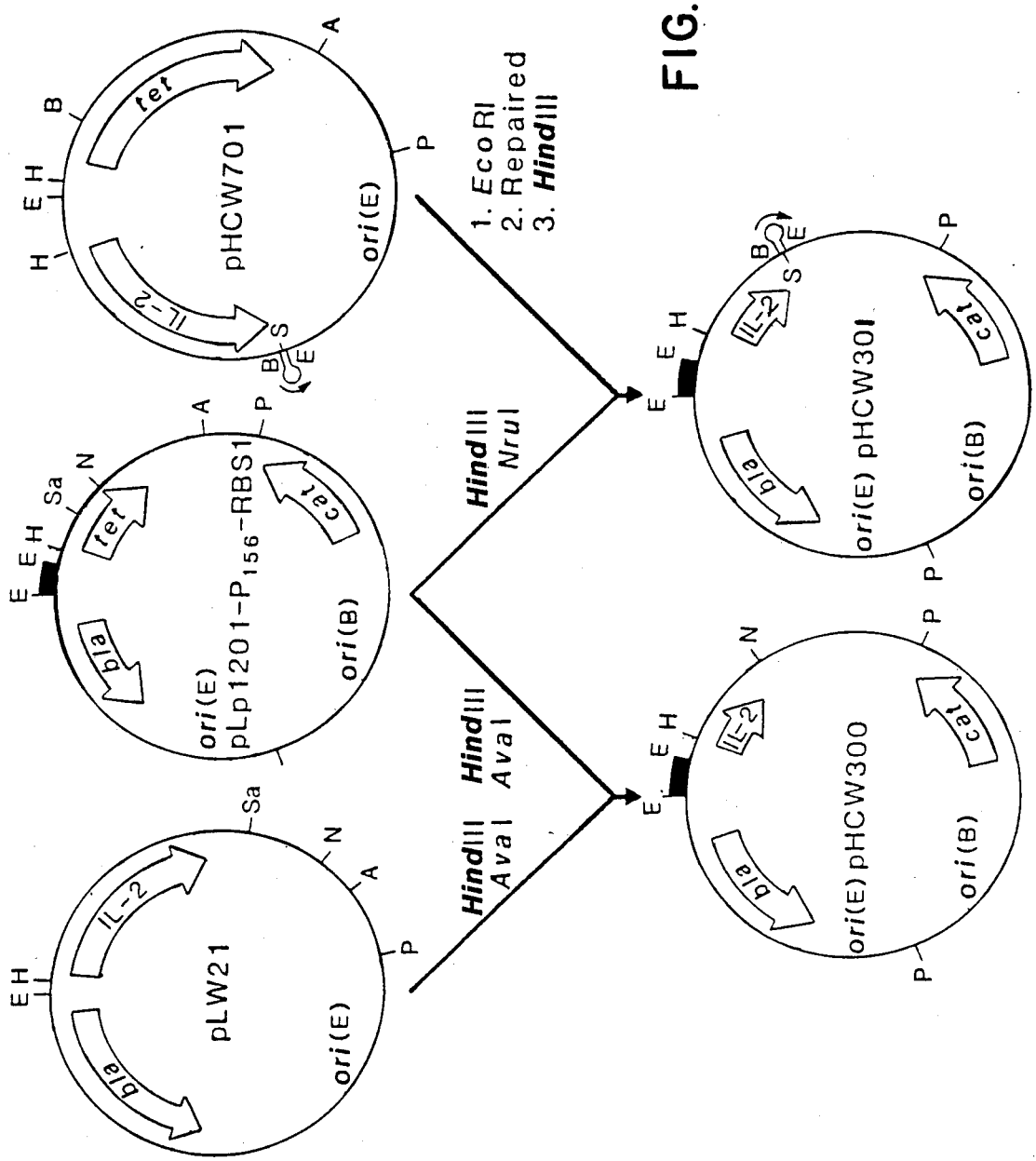

Plasmid pSYC677 is capable of replication in *E. coli* and *B. subtilis* (see FIG. 3). It contains the gene for prepenicillinase (penP) from *B. licheniformis* 749/C which is expressed under the influence of a specifically mutated signal sequence for penP in *E. coli* and *B. subtilis* that have been transformed with the plasmid. Mature penicillinase is secreted extracellularly into the medium by *B. subtilis* transformed with pSYC667. Mature penicillinase is secreted into the periplasmic space of *E. coli* transformed with pSYC667 and can be released from the periplasmic space by osmotic shock according to the method of Nosel and Heppel, *J. Biol. Chem.*, 241: 3055-3062 (1966) or Lunn and Pigiet, *J. Biol. Chem.*, 257: 11424-11430 (1962).

pSYC667 was constructed as follows:

*B. licheniformis* penicillinase gene has been sequenced. See Kroyer, J., and Chang, S., *Gene*, 15: 343-347 (1981), and Neugebauer, K., et al., *Nucl. Acids Res.*, 9: 2577-2588 (1981). The native signal sequence contains the codon TGC which codes for a cysteine at amino acid position 27. The cysteine residue at position 27 is modified as part of a sequence of events leading to formation of the membrane-bound lipoprotein form of penicillinase. See Nielsen, J. B. K., Caulfield, M. P., and Lampen, J. O., *Proc. Natl. Aca. Sci. (USA)*, 78: 3511-3515 (1981), and Lai, J. S., Sarvas, M., Brammar, W. J., Neugebauer, K., and Wu, H. C., *Proc. Natl. Aca. Sci. (USA)*, 78: 3506-3510 (1981). To specifically alter this biosynthetic pathway, and shunt more of the protein to the extracellular form secreted from the cell (in the case of Gram positive bacteria such as *B. subtilis*) or into the periplasmic space (in the case of Gram negative bacteria such as *E. coli*), it is necessary to mutate the sequence in the penicillinase signal sequence gene coding for cysteine at this position.

Because of its simplicity and efficiency, the method of primer-directed mutagenesis (see Zoller, M. J., and Smith., M., *Nucl. Acids Res.*, 10: 6487-6500 (1982)) was used for the construction of the cysteine to serine mutation. A DNA fragment containing wild-type penicillinase (penP) gene sequence was isolated. Specifically the DNA fragment located between the HindIII and BamHI sites was excised from plasmid pSYC310-2. See McLaughlin, et al. *Nucl. Acids Res.*, 3905-3919 (1982). Plasmid pSYC310-2 is capable of replicating in both *B. subtilis* and *E. coli*. It carries the wild-type penP gene from *B. licheniformis* 749/C on the HindIII-BamHI fragment. Those skilled in the art will realize that the wild-type penP gene could have been excised from other engineered recombinant plasmids that carry it. One such plasmid is *B. subtilis* plasmid pOG2165. The excised HindIII-BamHI DNA fragment from pSYC310-2 was purified by acrylamide gel elution and then ligated to RF DNA of coliphage M13mp9. See Viera, J., and Messing, J., *Gene*, 19: 259-268 (1982) and Messing, J., and Viera, J., *Gene*, 19: 269-276 (1982).

Specifically the purified HindIII-BamHI fragment from pSYC310-2 was ligated to M13mp9, obtained from Bethesda Research Laboratories, Inc., P.O. Box 577, Gaithersburg, Md., that had previously been digested with restriction endonucleases HindIII and BamHI. The double-stranded phage DNA was transformed into *E. coli* JM103, and the cells were cultured. A clone transformed with recombinant phage carrying the penP gene, i.e., recombinant phage M13-CM1, was identified and single-stranded phage DNA was prepared from this clone. The methods used are described in Zoller, M. J., and Smith, M., *Nucleic Acids Res.*, 10: 6487-6500 (1982).

A 15-nucleotide synthetic fragment 5'-GTTAGC-GGATCCTGC-3', made by the phosphotriester method of Narang, S. A., Hsiung, H. M., and Brousseau, R., in *Methods in Enzymology*, 68: 90-97 (R. Wu, editor) Academic Press (1979), was first phosphorylated at the 5'-end with ATP and T4 polynucleotide kinase and then employed as a primer to initiate the synthesis of the complementary strand in vitro after the 5'-phosphorylated primer had been annealed to the template M13-CM1 DNA. The primer was extended using DNA polymerase I Klenow fragment with all four dNTP's in the presence of T4 ligase. This primer complements the anti-sense strand of the penP signal sequence gene segment corresponding to the codons for the five amino acids from positions 25 to 29, except that the middle nucleotide in the synthetic primer is a mismatched nucleotide, that does not complement the corresponding nucleotide, G, in the wild-type penP gene template. Incorporation of the mismatched sequence into the penP gene causes conversion of the cysteine (TGC codon) to serine (TCC codon) at position 27.

The alteration on the encoded peptide is essentially a conversion of the —SH group on the cysteine$_{27}$ to the —OH group of the serine$_{27}$. At the nucelotide level, a mutant gains a BamHI site (GGATCC) and loses the HhaI (GCGC) at the mutation locus. The presence of a new BamHI site was the phenotype used to identify the mutants carrying the "G to C" nucleotide mutation.

In constructing the cysteine to serine mutation, complementary (minus) strands were synthesized by primer-extension reaction using Klenow fragment of *E. coli* DNA polymerase I on the M13-CM1 phage DNA template. See Zoller, M. J., and Smith, M., *Nucl. Acids Res.*, 10: 6487-6500 (1982). In the presence of T4-DNA ligase in this reaction, a fraction of the DNA molecules was converted to double-stranded, covalently-closed relaxed circles. These molecules were separated from other molecules, which either were incompletely extended by polymerase or failed to be ligated due to the incomplete kinase reaction of the primer. Separation was accomplished by agarose gel electrophoresis. This was carried out by applying the reaction mixture on a 0.8% agarose gel in the presence of 2 micrograms/ml of ethidium bromide. The band containing covalently closed circular DNA was excised and DNA recovered.

Plasmid pSYC667 is the same as pSYC660 except that, in place of the BamHI recognition sequence (5'-GGATCC-3') at the end of the approximately 1320 bp HindIII-BamHI fragment in pSYC660, pSYC667 has the sequence 5'-GGATCGATCC-3'.

Plasmid pSYC667 retains the PstI and BglII recognition sites of plasmid pSYC660. Similarly, the HindIII-BamHI fragment of M13penPS$_{27}$P$_{28}$ that contains the penPS$_{27}$P$_{28}$ gene has a PstI site and BglII site at the same locations as the PstI site and BglII site, respectively, in the HindIII-BamHi-penPS$_{27}$-containing fragment in pSYC667.

pSYC667 has been deposited at the ATCC under the terms of the Budapest Treaty and has been assigned ATCC No. 39758.

B. pHCW3-A3

Plasmid pSYC667 was digested with BclI, which cuts between the translation termination codon and transcription termination signal in the *B. licheniformis* penicillinase gene. The BclI ends were filled in using DNA polymerase I Klenow fragment and the four dNTP's. Such methods are well known to those skilled in the art (see Maniatis, et al., surpa (1982)). Enzymes were inactivated by phenol extraction and the DNA was recovered by ethanol precipitation.

The DNA was then further digested with NruI, and extracted twice with phenol and then twice with ether. NruI cuts downstream of the transcription termination signal of the *B. licheniformis* penicillinase gene in pSYC667. Thus, the large NruI-BclI cleaved fragment of pSYC667 contains the entire penicillinase gene through the translation termination codon but not including the transcription termination signal (see FIG. 3).

M13mp9 NP3 was cut with EcoRI and BamHI and a 400 bp fragment was isolated with standard methods using a 1% agarose gel and purified with DE-52 chromatography. Such methods are described in Maniatis, et al. supra, 104 (1982).

The EcoRI-BamHI 400 bp fragment from M13mp9 NP3 was then ligated into the large NruI-BclI fragment of pSYC667 using standard procedures. The resulting plasmids were transformed into *E. coli* K-12/CS412 using the method of Cohen et al. (*Proc. Natl. Acad. Sci. (USA)*, 69: 2110 (1973); see also Maniatis et al. supra, 1982, p. 250). Transformants were selected for resistance on LB medium plates containing 50 μg/ml ampicillin. Maniatis et al. supra, 440 (1982). Plasmid DNA was prepared from selected transformants by the mini-prep method of Birnboim and Doly (*Nucl. Acids Res.*, 7: 1513 (1979)) and was screened for a plasmid with the expected 1.6 kb EcoRI fragment, approximately 0.4 kb of the fragment derived from M13mp9 NP3 and approximately 1.2 kb from pSYC667. One transformant harbors a plasmid which was designated pHCW-A3.

B.1. Transformation of *B. subtilis* with pHCW-A3 pHCW-A3 was also transformed into *B. subtilis*, PSL1, Bacillus Genetic Stock Center No. IA510 (Bacillus Genetic Stock Center, Department of Microbiology, Ohio State University, Columbus, Ohio, U.S.A.). *B. subtilis* PSL1 is Leu$^-$, Arg$^-$, Thr$^-$ and recE4.

A culture of *B. subtilis* PSL1 cells was made competent for transformation using a technique related to that described by Anagnostopoulos and Spizizen, *J. Bacteriol.*, 741–746 (1961).

10×Spizizen I Minimal Solution was prepared by mixing, in a total solution volume of 1 liter made up with distilled water, 20 gm (NH$_4$)$_2$SO$_4$, 140 gm K$_2$HPO$_4$, 60 gm KH$_2$PO$_4$ and 10 gm Na citrate.

Spizizen I Medium was prepared by mixing 2.05 ml of 1M MgSO$_4$; 6 ml of 50% (w/w) glucose; 5 ml of 10% (w/w) yeast extract; 5 ml of 2% (w/w) casein hydrolysate; for each amino acid required by the strain to be transformed, 2.5 ml of 1% (w/w) solution of the amino acid; 50 ml of 10×Spizizen I Minimal Solution; and enough distilled water to bring the solution volume to 500 ml. For *B. subtilis* PSL1, the required amino acids are threonine, arginine and leucine.

Spizizen II Medium was prepared by adding 0.25 ml of 1M CaCl$_2$ and 1 ml of 1M MgCl$_2$ to 500 ml of Spizizen I Medium.

30 ml of Spizizen I Medium was inoculated with a colony of spores of the *B. subtilis* strain to be transformed and was grown overnight (16–20 hours) at 37° C.

15 ml of the overnight culture were then inoculated into 135 ml of Spizizen I Medium in a 2800 ml flask and grown at 37° C. The optical density at 600 nm (O.D.) of the culture was measured after 1.5 to 2 hours, and then every 15 minutes until the culture was found to be in late log phase on the basis of an increase in O.D. of less than 5% between 15-minute O.D. readings.

50 ml of late log phase culture was then inoculated into 450 ml of Spizizen II Medium in a 2800 ml flask and grown at 37° C. for 1.5 hours. After the 1.5 hour growth, cells were spun down by centrifugation at 5000 rpm for 10 minutes at 4° C.

The pellet from centrifugation was then resuspended in 45 ml of supernatant, to which 6 ml of 80% (v/v) sterile glycerol was then added, just prior to freezing the culture in a dry ice-ethanol bath (−20° C.). The cells in the frozen culture were competent cells, suitable for transformation by the desired plasmid, as follows:

0.5 ml–0.6 ml of the frozen, competent-cell-containing culture was thawed on ice, and 5 microliter to 50 microliter of solution containing the plasmid to be transformed into the cells was combined with thawed culture. The resulting mixture was shaken at 37° C. for 2 hours, during which transformation of plasmids and expression of genes on them occurred.

Finally, for selection, small aliquots such as about 5 microliter to about 200 microliter of the culture of transformed cells were transferred to plates containing the desired antibiotic or antibiotics for selection.

A mini-prep of plasmid pHCW-A3 was prepared as described above from *E. coli* K-12/CS4-12 transformed with the plasmid. To 1 ml of culture of competent *B. subtilis* PSL1, 5 microliters of mini-prep plasmid DNA solution was added. The mixture was incubated at 37° C. for 2 hours. Aliquots of the mixture were then plated and incubated at 37° C. overnight on rich medium agar plates (beef extract, 1.5 g/liter; yeast extract, 3.0 g/liter; peptone, 6.0 g/liter; agar 15.0 g/liter) to which 5 micrograms/ml chloramphenicol had been added. A chloramphenicol-resistant colony was picked and inoculated into 5 ml of 2×LB medium containing 5 μg/ml chloramphenicol; the culture was incubated overnight at 37° C. with shaking.

Subcultures of cultures of *B. subtilis* PSL1 transformed with pHCW-A3, and prepared as above, have been deposited in the CMCC under collection number 2120.

C. pLW1

Plasmid pLW1 is a pBR322 derivative capable of replication in *E. coli* containing a tetracycline resistance gene the *E. coli* trp promoter, ribosome binding site (RBS) fragment and a 706 bp HindIII-PstI DNA fragment which includes the gene for human interleukin-2 (IL-2) (Rosenberg, S. A. et al. *Science,* 223: 1412–1415 (1984)). pLW1 has been deposited at the ATCC under terms of the Budapest Treaty and assigned ATCC No. 39405.

D. pLW45

Plasmid pLW45 is a pBR322 derivative capable of replication in *E. coli* containing a tetracycline resistance gene and the *E. coli* trp promoter. The plasmid contains, on a 706 bp HindIII-PstI fragment, a gene for a modified IL-2 protein.

pLW45 has been deposited at the ATCC under terms of the Budapest Treaty and assigned ATCC No. 39629.

The modified IL-2 it encoded by pLW45 and the uses of such modified IL-2 protein in treating human diseases involving suppression of the immune system are described in Belgian Patent Ser. No. 898,016, issued Nov. 14, 1983, which is incorporated herein by reference.

E. pHCW701 and pHCW702

The 400 bp EcoRI-BamHI restriction fragment carrying the transcription termination signal of the cry gene was excised from M13mp90 NP3 by digestion with EcoRI and BamHI restriction endonucleases under buffer conditions suggested by the supplier. The EcoRI-BamHI ends of the fragment were made blunt ended with Klenow PolI fragment and dNTPs. The blunt ended fragment containing the transcription terminal signal of the cry gene was isolated by acrylamide gel electrophoresis. The isolated blunt ended fragment was electroeluted and ligated using T4 ligase and ATP into plasmid pLW1 that had been previously digested with StuI restriction endonuclease.

Regardless of the orientation in which the blunt ended fragment carrying the transcription termination signal is recombined with the StuI ends of pLW1, both of the original EcoRI and BamHI sites will be regenerated. One orientation results in the BamHI site being located nearer to the 3' end of the IL-2 gene and the plasmid so characterized is designated pHCW701. (This orientation is similar to that found in the cry gene itself.) The other orientation results in the EcoRI site being nearer to the 3' end of the IL-2 gene and this recombinant plasmid is designated pHCW702 (FIG. 3). Due to the a symmetrical location of the inverted repeat sequence in the EcoRI-BamHI fragment as depicted in FIG. 1, the stem and loop structure of the positive retroregulatory element is located approximately 310 bp downstream of the BamHI site at the 3' end of the IL-2 gene in pHCW701. In pHCW702, the stem and loop structure of the positive retroregulatory element is approximately 30 bp downstream of the EcoRI site of the 3' end of the IL-2 gene.

pHCW701 and pHCW702 can be easily distinguished by digesting the plasmid DNAs with restriction enzyme EcoRI and determining the size of restriction fragments using acrylamide or agarose gel electrophoresis. EcoRI digested pHCW701 releases a 960-bp restriction fragment which contains the trp promoter-RBS cassette (108 bp), the IL-2 gene (450 bp) and the terminator (400 bp). However, EcoRI digested pHCW702 releases a 560-bp restriction fragment which just contains only the trp promoter-RBS cassette (108 bp) and the IL-2 gene (450 bp).

F. Construction of pHCW801 pHCW801 was constructed to assess the effect of the positive retroregulatory element on productin of the modified IL-2 by plasmid pLW45. Plasmid pHCW701 was digested with BamHI and the ends were made blunt with Klenow PolI fragment and dNTPs as previously described. The blunt ended BamHI fragment was digested with AvaI. The largest resulting fragment was 2.7 kb and had one blunt BamHI end and one AvaI end. This fragment was purified by 0.8% agarose gel electrophoresis, and contains the 3' expression enhancement sequence.

Plasmid pLW45 was digested with StuI and then AvaI restriction endonucleases. An approximately 2.3 kb fragment was purified from the digest by agarose gel electrophoresis, electroeluted, and ligated using T4 ligase and ATP, to the fragment having a BamHI blunt end and an AvaI end, derived from plasmid pHCW701, which contained the positive retroregulatory element. Tetracycline resistant transformants were analyzed by mini-prep isolation of plasmid DNA and screened for the presence of an EcoRI fragment including both the modified IL-2 gene and the retroregulatory element. Birnboim and Doly, supra (1979).

G. pHCW301

1. Promoter 156:

A promoter, recognized by *B. subtilis* vegetative RNA polymerase, which is located on a 240 bp HhaI restriction fragment of the bacteriophage SP82, was first discovered by DNA restriction fragment probe analyses and *B. subtilis* RNA polymerase binding and initiation assay. Jones, B. B., Chan, H., Rothstein, S.; Wells, R. D. and Reznikoff, W. S., *Proc. Natl. Acad. Sci. (USA),* 74: 4914–4918 (1979). The 240 bp HhaI fragment was isolated from the HhaI digested SP82 DNA by gel electrophoresis and the ends were made blunt by removal of unpaired nucleotides with S1 nuclease (2200/ml in pH 4.6 buffer containing 300 mM NaCl, 60 mM $SO_4$ and 50 mM Na acetate). Maniatis et al. supra at p. 140. The blunt end fragment was then cloned into the HincII site of M13mp7 RF DNA (obtained from Bethesda Research Labs) that had been previously digested with HincII restriction endonuclease. DNA sequence analysis indicated that a RBS sequence was located at the 3' end of the HhaI restriction fragment carrying the promoter sequence. To eliminate the RBS sequence, the 240 bp HhaI fragment was digested with AluI restriction endonuclease. A 150 bp HhaI-AluI restriction fragment was isolated by acarylamide gel electrophoresis. The promoter was known to be located on this 150 bp restriction fragment by DNA sequence analysis. The 150 bp restriction fragment was then subcloned into the HincII site of M13mp7 RF DNA which had been previously digested with HincII restriction endonuclease to form a phage designated M13mp7-p156.

2. The ribosome binding site:

Two synthetic oligonucleotides with the sequence: (1) 5'-CGATAAGAGGAGGTA-3' and (2) 5'-AGCTTACCTCCTCTTAT-3' were made.

500 picomoles of each oligonucleotide were mixed and phosphorylated with polynucleotide kinase and ATP. The phosphorylated oligonucleotides were then annealed at 68° C. for 1 hour and then at 37° C. for 3 hours. The annealed oligomer having the sequence

```
5'AGCTTACCTCCTCTAAT-3'
3'ATGGAGGAGATTAGC-5'
``` was then cloned into he ClaI-HindIII site of pUC8-41 using T4 ligase under ligation conditions at a molar ratio of the oligomer to vector of approximately 10 to 1. pUC8 is commercially available (Bethesda Research Laboratories, Gaithersberg, Md. USA) and was modified as follows to yield pUC8-41- pUC8 was digested with BamHI and the ends were made blunt with Klenow PolI fragment. White colonies of *E. coli* JM103 containing the recircularized BamHI repaired pUC8 were selected. Plasmid DNA from these transformants was linearized with PstI and the ends were trimmed with Klenow PolI fragment. This procedure restores the correct reading frame for lac Z and after ligation blue transformants of JM103 were selected. Since repair of to BamHI site generates a ClaI site in DNA prepared from a DNA methylase lacking (Dam-) *E. coli* host, pUC8-41 was confirmed by ClaI linearization. Restriction enzyme analysis and nucleotide sequence determination were used to determine that the constructed recombinant plasmid designated pUC8-41-RBSL was indeed carrying a single copy of the synthetic ribosome binding site.

3. Construction of pLP1201-p156-RBS1

The synthetic ribosome binding site in pUC8-RBS1 was recovered by EcoRI-HindIII double digestion of the plasmid and was isolated by acrylamide gel electrophoresis. The EcoRI-HindIII fragment was subcloned into plasmid pLP1201 that had been previously digested with EcoRI and HindIII restriction endonucleases to form pLP1201-RBS1. Ostroff, G. R. and Pene, J. M. *Mol. Gen. Genet.*, 193:306–311 (1984). *E. coli* strain CS412 was transformed with plasmid pLP1201-RBS1 using conventional methods. Cohen et al. supra (1973). *E. coli* transformants carrying the plasmid pLP1201-RBS1 were ampicillin resistant and tetracycline sensitive.

Promoter p156 was then excised from M13mp7-p156 RF DNA using EcoRI restriction endonuclease and subcloned into the EcoRI site of pLP1201-RBS1 that had been previously digested with EcoRI restriction endonuclease. The desired recombinant plasmid pLP1201-p156-RBS1 confers ampicillin and tetracycline resistance to the *E. coli* host CS412 transformed with the plasmid.

4. Construction of plasmid pHCW300 (pLP1201-RBS1-p156-IL-2)

pHCW300 was constructed from pLW21 and pLP1201-RBS1-p156. pLW21 is derived from pBR322 and contains a 570 bp EcoRI-BanII sequence including a region coding for IL-2. pLW21 was constructed by ligating the 570 bp EcoRI-BanII sequence, obtained by digesting pLW1 with EcoRI and BanII endonucleases, into pBR322 previously digested to completion with EcoRI and BanII. This EcoRI-BanII fragment replaces the 485 bp EcoRI-BanII fragment in pBR322 containing a portion of the tetracycline resistance gene to yield pLW21 which is tetracycline sensitive. pLW21 was digested with HindIII restriction endonuclease followed by digestion with NruI restriction endonuclease. Two fragments were generated and a HindIII-NruI fragment approximately 400 bp in length was isolated by arylamide gel electrophoresis. Plasmid pLP1201-RBS1-p156 was digested with HindIII and NruI restriction endonuclease to form a linearized plasmid with the region containing the tetracycline resistance gene removed. The linearized plasmid was combined with the 400 bp HindIII-NruI fragment from pLW21 and was ligated using T4 ligase to form a plasmid designated pHCW300 having the p156 promoter and RBS described above and a 400 bp sequence having a DNA sequence coding for IL-2. Tetracycine sensitive transformants of *E. coli* were obtained by replica plating of ampicillin resistance transformants and were screened for the presence of plasmid pHCW300 using HindIII and AvaI restriction endonucleases to generate two fragments of about 7 kb and 0.85 kb.

5. Construction of plasmid pHCW301 (pLP1201-RBS1-p156-IL-2-retroregulator)

Plasmid pHCW701 was digested with EcoRI restriction endonuclease and the ends were made blunt with Klenow Pol I fragment and dNTPs. Following digestion with HindIII restriction endonuclease, the approximately 0.85 kb fragment containing the IL-2 gene and the positive retroregulatory element was isolated by agarose gel electrophoresis. Plasmid pLP1201-RSS1-p156 was digested with HindIII and NruI restriction endonucleases resulting in the excision of the region containing the tetracycline resistance gene. The 0.85 kb EcoRI (blunt)-HindIII fragment containing the IL-2 gene and the positive retroregulatory element was ligated to the HindIII-NruI digested pLP1201-RBS1-p156 vector using T4 ligase under ligating conditions. Tetracycline sensitive transformants of *E. coli* were obtained by replic plating of ampicillin resistant transformants and were screened for the plasmid pHCW301 using EcoRI restriction endonuclease. Three fragments of approximately 7 kb, 0.88 kb, and 156 bp corresponding to the expected sizes for the pLP1201-RBS1-fragment, IL-2 gene-positive retroregulatory element fragment, and promoter fragment respectively, were generated.

EXAMPLE III

Enhanced Protein Expression by Genes into Which a Positive Retroregulatory Element Has Been Inserted A. Assay procedure for *B. licheniformis* penicillinase expression 1. In *E. coli*

Five ml of YT broth (8 g/l tryptone, 5 g/l yeast extract, 5 g/l NaCl) containing 50 µg/ml ampicillin were inoculated with individual colonies of *E. coli* K-12/CS412 carrying either pSYC667 or pHCW-A3 and were grown overnight at 37° C. with shaking in a New Brunswick rotary incubator. Cells were then pelleted at 5,000 rpm for 10 minutes in the JA-20 rotor of a Beckman Model J-21C centrifuge. The cell pellet was washed with 5 ml ice-cold 50 mM phosphate buffer pH 7.0. The washed cell pellet was resuspended into 0.5 ml 50 mM phosphate buffer and sonicated using a Branson 350 Sonifer at maximum output for 3 minutes in 0.5 second bursts at 0° C. The sonicate was spun in an Eppendorf microfuge for 2 minutes. The resulting supernatant was used for the assay of enzyme activity.

The production of *B. licheniformis* penicillinase was assayed using the chromogenic β-lactamase substrate PADAC (available from Cal Biochem) by the method of Schindler and Huber. Scindler, P. and Huber, G., "Use of PADAC, A Novel Chromogenic, β-Lactamase Substrate, for the Detection of β-Lactamase Producing Organisms and Assay of β-Lactamase Inhibitors/Inactivators", in *Enzyme Inhibitors,* Brodbeck, U., ed., Weinheim: VerlagChemice, 1980, p. 169-176. PADAC substrate (MW 562.7) was prepared by making a solution having $OD_{573}=1$ (about 27.4 μM) in phosphate buffer at pH 7.0. The decrease in absorbance at 573 nm over time, after the addition of the cell extract, was measured using a Cary 219 spectrophotometer at room temperature. The results are shown in Table I.

2. In *B. subtilis*

*B. subtilis* PSL1 was transformed with either pSYC667 or pHCW-A3, according to the method related to Anagnostopolus and Spizizen supra (1961) described above, plated on rich medium agar described above, and grown overnight at 37° C. Five ml of 2×LB medium containing 5 μg/ml chloramphenicol was inoculated with individual transformants and grown at 37° C. with shaking on a New Brunswick rotary incubator overnight. Cells were then pelleted at 5000 rpm for 10 minutes in a JA-20 rotor as above. The supernatant was used for the penicillinase assay by the same method described above for *E. coli*. The results are shown in Table I.

TABLE I

Production of the penicillinase polypeptide in *E. coli* and *B. subtilis* strains carrying penP recombinant plasmids with or without the positive retroregulatory element

| Host | Plasmid | Specific Activity of Penicillinase[1] |
|---|---|---|
| *E. coli* CS412 | — | 0 |
| | pSYC667 | 1055 |
| | pHCW-A3 | 2762 |
| *B. subtilis* 1A510 | — | 0 |
| | pSYC667 | 3280 |
| | pHCW-A3 | 17510 |

[1]Specific activity is defined as nmoles of PADAC hydrolyzed per minute per mg of protein at 25° C.

Assay procedure for IL-2 expression

1. In *E. coli*

A shake flask culture of *E. coli* K12/MM294 transformed with pHCW701, pHCW702, or pLW1 were grown in 10 ml of tryptophan (trp) containing N medium (0.7% $Na_2HPO_4$, 0.3% $KH_2PO_4$, 0.5% NaCl, 0.1% $NH_4Cl$, 0.2% glucose, 0.5% casamino acids, 40 μg/ml trp, and 10 μg/ml tetracycline) at 37° C. overnight with shaking in a New Brunswick rotary incubator. Cells from a 5 ml overnight culture were pelleted by centrifugation at 5000 rpm for 10 minutes in a JA-20 rotor. The cell pellet was resuspended in 5 ml of N medium without trp containing 2 μg/ml thiamine. Optical density was determined by absorbance at 600 nanometers ($OD_{600}$) in a spectrophotometer. 25 ml subcultures having an $OD_{600}$ of 0.05 in N medium minus trp were set up and grown at 37° C. with shaking to a final $OD_{600}$ of about 0.3. Controls were set up and grown under the same conditions except that the N medium had tryptophan. Cells were then pelleted and resuspended in IL-2 sonication buffer (50 mM Tris, pH 7.5, 50 mM EDTA, 15% sucrose, 1% SDS) to a final $OD_{600}=10$. Cells were sonicated as described above. Supernatants were assayed for the presence of IL-2 activity by the methods described in Gillis, S., et al. *J. Immunol.,* 120, 2027-2032 (1978). Results are shown in Table II.

2. Fermentation cultures

*E. coli* K-12/MM294-1 transformed with either pHCW801 or pLW45 was fermented in a 10 liter fermentor at 37° C. and 350-1200 rpm with 0-2 liters per minute (1 pm) air and 0.1 pm oxygen (dissolved oxygen at about 40%). The medium consisted of 72 mM $(NH_4)_2SO_4$, 21.6 mM $KH_2PO_4$, 1.5 mM $Na_3$ citrate, 1.5 mg/l TK-9 Trace elements, and the following sterile additons: 3 mM 0.5% $MgSO_4$, 20 mg/l 1% thiamine-HCl, 72 mM 0.2M $FeSO_4$, 5 g/l 50% glucose, 70 mg/l 0.5%, L-tryptophan, 5 mg/l 1% tetracycline, and 100 ml/l 20% casamino acids (added at $OD_{680}=15-20$). The inoculum was 20 mg/l and the pH was controlled at 6.8 with 5N KOH. A glucose feed was also employed to maintain glucose concentration between 5-10 g/l.

Culture samples for SDS polyacrylamide gel electrophoretic analysis of total cell protein were withdrawn hourly from 13.7 hours to 19.7 hours. Densitometry of protein bands of the gels indicated a maximum production of IL-2 as 17.2% of total cell protein at 17.7 hours. The biological activity of IL-2 from these samples was determined as previously described for IL-2 expression in *E. coli*. Results are shown in Table II.

3. In *B. subtilis*

Cultures of *B. subtilis* 1A510 transformed as described above with pHCW301 or pHCW300 were grown to an $OD_{600}=1.0$ at 37° C. with shaking after single colony inoculation into 5 ml of 2×LB medium containing 5 μg/ml chloramphenicol. Cells were pelleted, resuspended in IL-2 sonication buffer, sonicated and assayed for IL-2 activity, as described for *E. coli*. Results are shown in Table II.

TABLE II

Production of IL-2 and modified IL-2 with and without the positive retroregulatory element 1. In *E. coli* (5 ml culture)

| Transformed with | Induction | Specific Activity of IL-2 Produced (U/150 μg total Cellular Protein) |
|---|---|---|
| pLW1 | — | $<7 \times 10^3$ |
| | + | $2 \times 10^5$ |
| pHCW701 | — | $2.8 \times 10^4$ |
| | + | $1.4 \times 10^6$ |
| pHCW702 | — | $1.5 \times 10^5$ |
| | + | $9.2 \times 10^5$ |

2. In *E. coli* (10 l Fermentor)

| Transformed with | IL-2 Produced (U/g dry weight) |
|---|---|
| pLW45 | $8.95 \times 10^7$ |
| pHCW801 | $1.6 \times 10^8$ |

3. In *B. subtilis* (5 ml culture)

| Transformed with | Specific Activity of IL-2 Produced (U/150 μg Total Cellular Protein) |
|---|---|
| pHCW300 | $1 \times 10^4$ |
| pHCW301 | $2.5 \times 10^4$ |

EXAMPLE IV

Deletion Mapping of the Positive Retroregulatory Element

Deletion studies were carried out to define more precisely the sequence within the cry terminator region responsible for the positive retroregulatory effect. Oligodeoxyribonucleotide-directed site-specific mutagenesis according to the method of Zoller, M. and Smith, M., Oligonucleotide-directed mutagensis of DNA fragments cloned into M13 vectors *Methods in Enzymology,* 100: 468-500 (1983) was employed to introduce two BglII restriction sites separately at the locations 80- and 20-bp upstream from the inverted repeat sequence in the cry terminator fragment depicted respectively as B1 and B2 in FIG. 1. These shortened terminator-containing fragments can be excised from the respective, modified M13mp9 and NP3 phage genomes by BglII-EcoRI digestion. They were cloned into pSYC667 at the BclI-NruI site by the procedures similar to that employed for the construction of pHCW-A3, and generated plasmids pHCW-A4 and pHCW-A5. Data on the analysis of B. subtilis as well as E. coli strains harboring these plasmids for their ability to express the cloned penP gene are presented in Table III. It is clear that the shortened fragments still contain the positive retroregulatory element observed in the original fragment. Since the two newly created BglII sites are outside of the cry coding sequence, this data demonstrates that the locus that confers the enhancing activity is located in the non-coding region of the cry gene, and it probably overlaps with the terminator of cry gene.

B. subtilis strain PSL1 and E. coli strain CS412 were transformed with plasmids pHCW-A3, pHCW-A4, or pHCW-A5 as described above. Penicilinase activity, assayed as described above is shown in Table III.

TABLE III

Synthesis of Penicillinase in E. coli and B. subtilis Strains Carrying the penP-cry Fusion Plasmids[1]

| Host Strain | Plasmid | Length of cry-derived Fragments | Specific Activity of Penicillinase[1] |
|---|---|---|---|
| E. coli CS412 | pHCW-A3 | 380 | 2762 |
|  | pHCW-A4 | 158 | 2631 |
|  | pHCW-A5 | 78 | 2861 |
| B. subtilis 1A510 | pHCW-A3 | 380 | 17510 |
|  | pHCW-A4 | 158 | 18600 |
|  | pHCW-A5 | 78 | 17822 |

[1]Penicillinase was assayed as described in Table 1.

EXAMPLE V

Insertion of Positive Retroregulatory Element Increases the Level of Production of a Novel Recombinant IL-2 Mutein using a Portable Temperature Regulated Control Cassette in a Temperature Regulated ColE1 Copy Mutant Plasmid Vector A. Construction of plasmid pFC54.t Plasmid pFC54 encodes des-Alanyl, serine$_{125}$ interleukin-2 (IL-2) under the control of the bacteriophage λ P$_L$ promoter and gene N ribosome binding site (P$_L$ N$_{RBS}$). The ColE1 plasmid vector contains two mutations which confer a temperature sensitive copy number phenotype on the plasmid. E. coli cells harboring this plasmid have been thermally induced to accumulate 20% of the total protein as a novel IL-2 mutein.

Plasmid pFC54 was digested to completion with SphI and treated with DNA polymerase I (Klenow fragment) in the presence of 25 μM dGTP to eliminate the 3' protruding single stranded tail. The blunt-ended DNA was subsequently digested with XbaI.

Plasmid pHCW801 was digested to completion with EcoRI, treated with DNA polymerase I (Klenow fragment) in the presence of dNTPs, and subsequently digested with XbaI. The 655 bp DNA fragment comprising the C-terminal 225 bp of ser$^{125}$ IL-2, 36 bp of 3' untranslated IL-2 cDNA and 394 bp of the fragment carrying the positive retroregulatory element were purified by gel electrophoresis. The pFC54 vector DNA fragments and purified pHCW801 fragment were ligated (1:3 molar ratio) at a concentration of 30 μgDNA/ml DNA using T4 DNA ligase under conditions favoring ligation of sticky ends, diluted 2.5 fold and then ligated using T4 DNA ligase under blunt-end ligation conditions to favor intramolecular circle formation. The ligated DNA was digested with BanII to inactivate undesired ligation products comprised of the small and large XbaI-SphI fragments of pFC54.

E. coli K12 strain DG95(λN$_7$N$_{53}$cI857susP80) was tranformed to Amp$^R$ with 60 ng of the ligated and digested DNA. This strain contains a lambda prophage which encodes a temperature-sensitive λ CI repressor, which at low temperature (30°-32° C.) is active. However, at high temperature (36°-42° C.) the repressor is inactive and transcription from the P$_L$ promoter can proceed. It is further characteristic of this strain that at elevated temperatures the prophage fails to induce. Transformants were selected for Amp$^R$ and Amp$^R$ colonies were screened for the desired 5.6 kb plasmid. Candidate plasmids were screened for release of an 1182 bp EcoRI fragment (ligation of repaired EcoRI site in the fragment carrying the positive retroregulatory element to the repaired SphI site in the vector fragment was expected to regenerate an EcoRI site), retention of the XbaI site within the IL-2 coding sequence, acquisition of a unique BamHI site (in the terminator fragment), and loss of the unique BanII site in pFC54. A desired recombinant plasmid was isolated and was designated pFC54.t.

As shown below, when E. coli K12 strain DG95(λN$_7$N$_{53}$cI857susP80) harboring plasmid pFC54.t is temperature-induced under the proper conditions, 34% of the total cellular protein is des-Alanyl, Ser$^{125}$ IL-2.

Plasmid pFC54.t has been deposited pursuant to the Budapest Treaty in the ATCC under accession number 39789.

Figure 6:
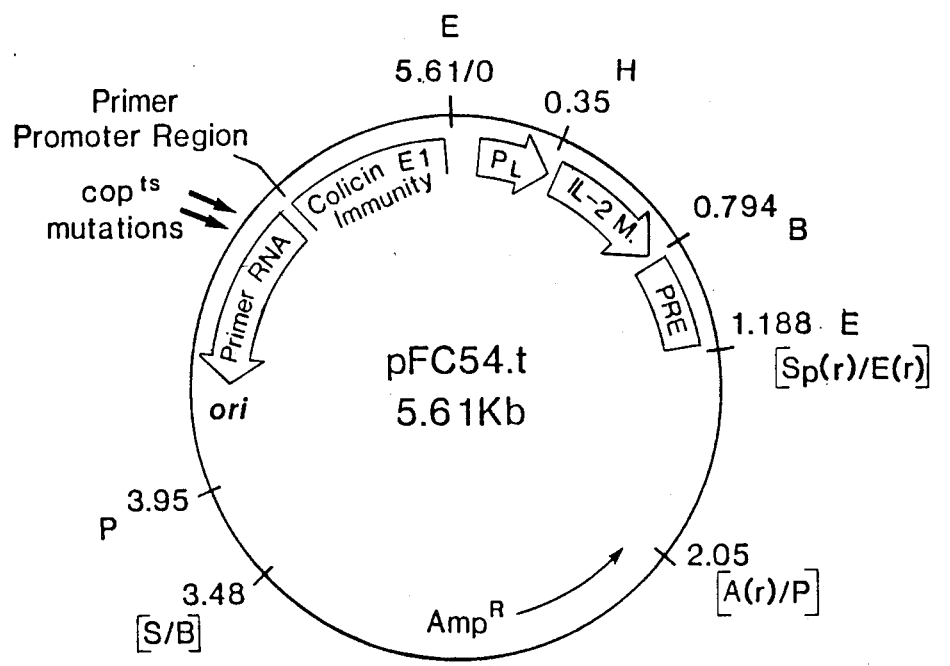
Figure 7B:
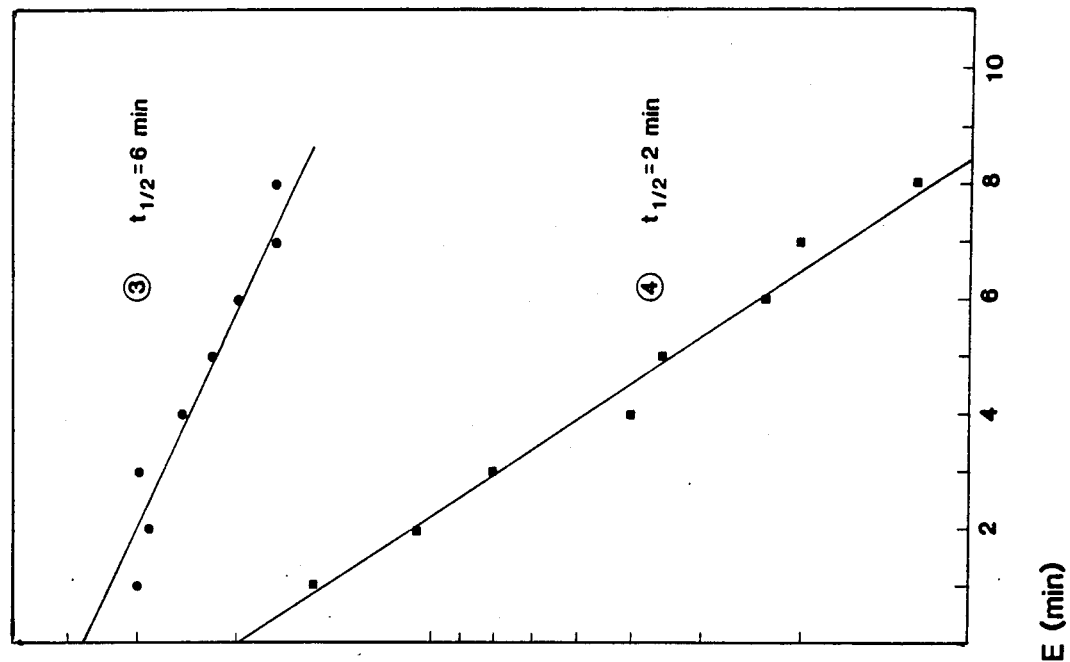
Figure 7A:
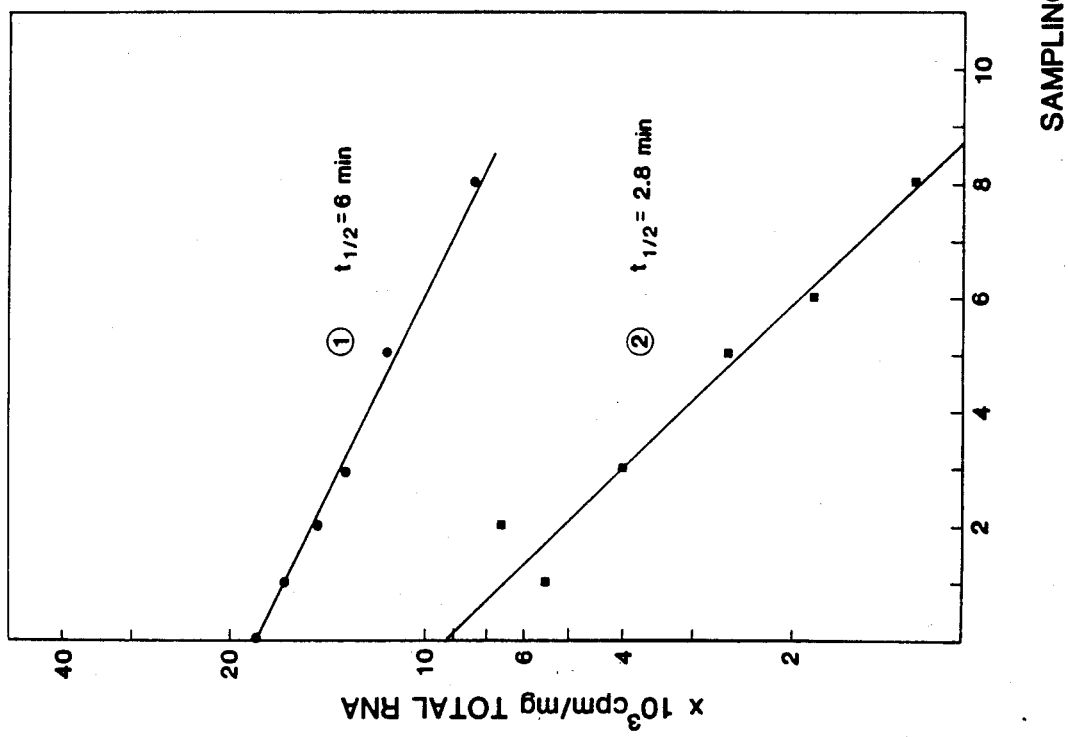

Plasmid pFC54.t is shown in FIG. 6. Beginning with the EcoRI restriction endonuclease site designed 5.61/0 and moving in a clockwise direction, plasmid pFC54.t comprises the components described immediately below.

Coordinate 0-0.35 kb comprise an EcoRI-HindIII module encoding the temperature regulated promoter-/operator of the bacteriophage λ PL promoter and the adjacent gene N ribosome binding site. The BglII recognition site at λ coordinate 35715 (Sanger, F. et al., J. Mol. Biol., 162: 729-773 (1982)) has been converted to an EcoRI recognition site and the HinfI recognition site at λ coordinate 35366 has been converted to a HindIII recognition site for insertion into plasmid pFC54.t.

Coordinates 0.35-0.794 kb comprise the 444 bp HindIII-StuI fragment of plasmid pLW46 encoding mture human des Alanyl, Ser$^{125}$ IL-2 mutein. Wang, A. et al., Science, 224: 1431-1433 (1984).

The 5' HindIII site immediately precedes the ATG initiation codon of the altered mutein (Rosenberg, S. A. et al. Science, 223: 1412-1416 (1984) and the StuI recognition site (36 bp distal to the opal stop codon in human IL-2) has been converted to a BamHI recognition site in pFC54.t.

Coordinates 0.794-1.188 kb comprise the 394 bp BamHI-EcoRI DNA fragment from plasmid pHCW801 and includes the positive retroregulatory element from the B. thuringiensis delta enotoxin gene.

Coordinates 1.188-2.05 kb comprise the 863 bp SphI (repaired)/AvaI (repaired) pBR322 DNA fragment (pBR322 coordinates 567-1429, respectively).

Coordinates 2.05–3.48 kb comprise the 1.43 kb PvuII-BamHI DNA fragment from plasmid pOP6 (Gelfand, D. H., et al., *Proc. Natl. Acad. Sci. USA*, 75: 5869–5873, 1978; Muesing, M., et al., *Cell*, 24: 235–242, 1981) encoding the β-lactamase gene of bacterial transposon Tn3. Heffron, F., et al., *Cell*, 18: 1153–1163 (1979).

Coordintes 3.48–3.95 kb comprise the 0.47 kb SstI-PvuII DNA fragment of pOP6 (Gelfand, supra 1978). This DNA fragment contains the left boundary of bacterial transposon Tn3 (coordinate 1-270, Heffron, F., et al. supra 1979) and a portion of the adjacent ColE1 HaeII C fragment.

Coordinates 3.95–5.61 kb comprise the 1.66 kb PvuII-EcoRI DNA fragment from plasmid pEW27 (Wong, E. M., et al., *Proc. Natl. Acad. Sci. USA*, 79: 3570–3574 (1982)). This fragment encodes the colicin E1 immunity region of plasmid ColE1 as well as the primer promoter region, RNA I region, and origin of replication. The wild-type ColE1 DNA sequence of pBGP120 (Polisky, B., et al., *Proc. Natl. Acad. Sci. USA*, 73: 3900–3904 (1976) and Gelfand, D. H., et al., supra (1978) has been altered at two positions (G→A transitions in the DNA strand corresponding to nucleotides 125 and 135 of the primer RNA transcript) conferring a temperature sensitive Cop-phenotype on the plasmid pFC54.t B. IL-2 mutien produced by the transformed strains

*E. coli* K12 strain DG95 ($\lambda N_7 N_{53} cI857 susP80$), transformed with either pFC54 or pFC54.t, using methods described above were grown in 10 liter fermentors under the same conditions as described above for 18.5 hours to an $OD_{680}$ of 28.7 or 28.1 respectively. Following measurement at 18.5 hours, the temperature of the culture medium containing transformed microorganism was raised to 42° C. to induce the temperature sensitive copy number plasmid and derepress the promoter. Samples were taken at half hourly or hourly intervals after induction for 4 hours. Each sample was pelleted by centrifugation and was resuspended to a concentration of 10 mg dry weight (dw)/ml in phosphate buffered saline (PBS). Each sample was then diluted 10× in 1% sodium dodecyl sulphate/PBS, sonicated in a Heat Systems Model W-375 sonicator for a period sufficient to completely disrupt the cells and assayed. Units of IL-2 mutien/ml was determined in the manner described above. Mg protein/ml sonicate was determined by the Lowry method. Units IL-2 mutien/mg protein was determined and is reported in Table IV below.

The production of IL-2 as a percentage of total cellular protein produced for each sample was determined by SDS acrylamide gel electrophoresis. Approximately equal amounts of protein as determined by the Lowry assay were loaded onto the gel. Bands were stained with Coomasie Blue strain and were read using a Zeineh scanning densitometer attached a Hewlet Packard 3390A integrator. Pecent IL-2 mutien was determined by the integration program. Il-2 mutien production as a percentage of total cellular protein is reported in Table V below. Percent increase in Il-2 was found by determining the net increase in IL-2 mutien produced by the strain carrying the positive retroregulatory element and expressing the increase as a percentage of the IL-2 mutien produced by the strain without the positive retroregulatory element.

*E. coli* strain K12 DG95 ($\lambda N_7 N_{53} cI857 susP80$) transformed with pFC54.t was grown under the same conditions as described above except that the culture was temperature induced at an $OD_{680}$ of 14.0 rather than 28.1 as in the previous example. Samples were taken and determinations were made as in the previous example. IL-2 mutien production as a percentage of total cell protein was determined to be 34% of total cellular protein. Increased production of IL-2 mutien by the microorganism transformed with the plasmid carrying the positive retroregulatory element is best accomplished when temperature induction is carried out at lower cell density as measured by $OD_{680}$ (14) than higher $OD_{680}$ (28.1).

TABLE IV

| Time after Induction | U IL-2/mg Protein | | % Increase U IL-2/mg Protein |
|---|---|---|---|
| | *E. coli* with pCF54 | *E. coli* with pCF54.t | |
| 0 | $715 \times 10^4$ | $8.60 \times 10^4$ | 10.3 |
| 1 hr. | $1.44 \times 10^5$ | $1.62 \times 10^5$ | 12 |
| 1.5 hr. | $1.99 \times 10^5$ | $2.26 \times 10^5$ | 13.5 |
| 2 hr. | $2.54 \times 10^5$ | $2.68 \times 10^5$ | 5.5 |
| 3 hr. | $2.23 \times 10^5$ | $3.02 \times 10^5$ | 26.1 |
| 4 hr. | $2.85 \times 10^5$ | $2.52 \times 10^5$ | — |

TABLE V

| | IL-2 Mutien % Total Cellular Protein | | |
|---|---|---|---|
| Time | pFC54 | pFC54.t | % Increase |
| 0 hr. | 3.3 | 2.6 | — |
| 0.5 hr. | 12.3 | 12.7 | 2 |
| 1 hr. | 14.7 | 17.9 | 21 |
| 2 hr. | 24.3 | 21.5 | — |
| 3 hr. | 21.6 | 20.6 | — |
| 4 hr. | 23.8 | 22.4 | — |

Deposited Strains

Deposits of strains listed in the following Table VI are stored in the Master Culture Collection of Cetus Corporation, the assignee of the present application, Emeryville, Calif., U.S.A., and have been assigned the Cetus Master Culture Collection numbers listed in the Table. The listed strains were also deposited by Cetus Corporation with the American Type Culture Collection, Rockville, Md., U.S.A., on the dates indicated in the Table and were assigned the ATCC numbers listed in the Table. The ATCC deposits were made under the Budapest Treaty on the International Recognition of Deposits of Microorganisms for Purposes of Patent Procedures and the Regulations promulgated thereunder, and the strains will be available to the public in accordance with the terms of said Treaty and Regulations.

TABLE VI

| Strain | Plasmid | ATCC Deposit Number |
|---|---|---|
| *E. coli* K-12/CS412 | pSYC667 | 39758 |
| *B. thuringensis* HD-1 | | 1615 |
| *E. coli* K-12/MM294 | pHCW701 | 39757 |
| *E. coli* DG95 (g) | pFC54.t | 39789 |
| *E. coli* MM294 | pLW1 | 39405 |
| *E. coli* MM294-1 | | 39626 |
| *E. coli* MM294 | - | 39452 |

Various modifications of the invention, as described and exemplified in the present specification, will be apparent to persons of skill in the art. It is intended that such modifications are within the scope of the invention and the appended claims.

We claim:

1. A plasmid vector comprising a first DNA sequence expressionable for a selected gene product, a positive retroregulatory element comprising a DNA sequence which transcribes for a corresponding RNA transcript which is capable of forminfg a stem and loop structure having a Gibbs free energy constant of a about −30.4 Kcal ligatged to said first DNA sequence in a relationship thereto whereby expression of said selected gene product is enhanced, a second DNA sequence which is the $P_L$ promoter operably linked to a third DNA sequences corresponding to an N gene ribosome binding site said second and said third DNA sequences operably linked to said first DNA sequence expressionable for a selected gene product.

2. The plasmid vector of claim 1 wherein said first DNA sequence expressionable for a selected gene product encodes IL-2.

3. The plasmid vector of claim 1 wherein said first DNA sequence expressionable for a selected gene product encodes an active cysteine depleted IL-2.

4. The plasmid vector of claim 1 wherein said first DNA sequence expressionable of a selected gene product encodes desalanyl ser$^{125}$ IL-2.

5. The plasmid vector of claim 4 wherein said plasmid vector is a temperature sensitive copy number mutant.

6. The plasmid vector of claim 1 wherein said positive retroregulatory element comprises a portion of the 3' flanking sequence of the Bacillus thuringiensis crystal protein gene wherein said portion of said flanking sequence includes an inverted repeat sequence.

7. The plasmid vecotr of claim 6 wherein said first DNA sequence expressionable for a selected gene product encodes desalanyl ser$^{125}$ IL-2.

8. The plasmid vector of claim 7 wherein said plasmid vector is a temperature sensitive copy number mutant.

9. A cell transformed with the plasmid vector of claim 1.

10. The cell of claim 9 wherein said cell is an E. coli strain comprising a λ prophage which encodes a temperature sensitive λ cI repressor which is active at temperatures between 30°–32° C. and inactive at temperatures between 36°–40° C. said prophage failing to induce at temperatures between 36°–42° C.

11. The cell of claim 10 wherein said E. coli strain is DG95(λN$_7$N$_{53}$cI857susP80).

12. An E. coli cell transformed with the plasmid vector of claim 5 wherein said cell is an E. coli strain containing a λ prophage which encodes a temperature sensitive λ cI repressor which is active at temperatures between 30°–32° C. and inactive at temperatures between 36°–42° C. said prophage failing to induce at temperatures between 36°–42° C.

13. The E. coli cell of claim 12 wherein said E. coli strain is DG95(λN$_7$N$_{53}$cI857susP80).

14. An E. coli cell transformed with the plasmid vector of claim 8 wherein said cell is an E. coli strain containing a λ prophage which encodes a temperature sensitive λ cI repressor which is active at temperatures between 30°–32° C. and inactive at temperatures between 36°–42° C. said prophage failing to induce at temperatures between 36°–42° C.

15. The E. coli cell of claim 14 wherein said E. coli strain is DG95(λN$_7$N$_{53}$cI857susP80).

16. Plasmid pFC54.t.

17. E. coli strain DG95(λN$_7$N$_{53}$cI857susP80) transformed with plasmid pFC54.t.

* * * * *